United States Patent
Catena Ruiz et al.

(10) Patent No.: US 7,452,904 B2
(45) Date of Patent: Nov. 18, 2008

(54) 1-ALKYL-1-AZONIABICYCLO' 2.2.2 OCTANE CARBAMATE DERIVATIVES AND THEIR USE AS MUSCARINIC RECEPTOR ANTAGONISTS

(75) Inventors: Juan Lorenzo Catena Ruiz, L'Hospitalet de Llobregat (ES); Carles Farrerons Gallemi, Mataro (ES); Anna Fernandez Serrat, Sant Cugat del Vallès (ES); Ignacio José Miquel Bono, L'Hospitalet de Llobregat (ES); Dolors Balsa Lopez, Badalona (ES); Carmen Lagunas Arnal, L'Hospitalet de Llobregat (ES); Carolina Salcedo Roca, Corbera (ES); Natividad Toledo Mesa, Vilanova del Vallès (ES); Andrés Fernandez Garcia, Barcelona (ES)

(73) Assignee: Chiesi Farmaceutici S.p.A., Parma (IT)

( * ) Notice: Subject to any disclaimer, the term of this patent is extended or adjusted under 35 U.S.C. 154(b) by 213 days.

(21) Appl. No.: 10/499,130

(22) PCT Filed: Dec. 18, 2002

(86) PCT No.: PCT/EP02/14470

§ 371 (c)(1),
(2), (4) Date: Oct. 12, 2004

(87) PCT Pub. No.: WO03/053966

PCT Pub. Date: Jul. 3, 2003

(65) Prior Publication Data

US 2005/0043349 A1    Feb. 24, 2005

(30) Foreign Application Priority Data

Dec. 20, 2001   (ES) ................. 200200043

(51) Int. Cl.
*A61K 31/439* (2006.01)
*C07D 453/02* (2006.01)

(52) U.S. Cl. ................... 514/305; 546/137
(58) Field of Classification Search ........... 546/137, 546/135; 514/305
See application file for complete search history.

(56) References Cited

U.S. PATENT DOCUMENTS

| 6,916,828 B2 * | 7/2005 | Farrerons Gallemi et al. ............ 514/305 |
| 7,115,629 B2 * | 10/2006 | Farrerons Gallemi et al. ............ 514/305 |
| 7,208,501 B2 * | 4/2007 | Buil Albero et al. ........ 514/305 |

FOREIGN PATENT DOCUMENTS

| EP | 0 747 355 A1 | 12/1996 |
| EP | 0 801 067 A1 | 10/1997 |
| WO | 01/04118 A2 | 1/2001 |
| WO | WO 02/051841 | * 12/2001 |
| WO | 02/051841 A1 | 7/2002 |

* cited by examiner

*Primary Examiner*—Charanjit S Aulakh
(74) *Attorney, Agent, or Firm*—Merchant & Gould P.C.

(57) ABSTRACT

Carbamate of general formula (I), wherein R1, R2, and R3 are H, OH, $NO_2$, SH, CN, F, Cl, Br, I, COOH, $CONH_2$, $(C_1-C_4)$-alkoxycarbonyl, $(C_1-C_4)$-alkylsulfanyl, $(C_1-C_4)$-alkylsulfinyl, $(C_1-C_4)$-alkylsulfonyl, $(C_1-C_4)$-alkoxyl optionally substituted with one or several F, and $(C_1-C_4)$-alkyl optionally substituted with one or several F or OH; R4 is cycloalkyl, phenyl, heteroaryl or a bicyclic ring system; R5 is cycloalkyl, $(C_5-C_{10})$-alkyl, a substituted $(C_1-C_{10})$-alkyl; and $X^-$ is a physiologically acceptable anion. Carbamate (I) is selective $M_3$ receptor antagonists versus $M_2$ receptor and may be used for the treatment of urinary incontinence (particularly, the one caused by overactive bladder), irritable bowel syndrome, and respiratory disorders (particularly, chronic obstructive pulmonary disease, chronic bronchitis, asthma, emphysema, and rhinitis), as well as in ophthalmic interventions.

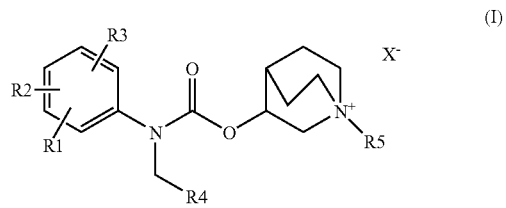

12 Claims, No Drawings

1-ALKYL-1-AZONIABICYCLO' 2.2.2 OCTANE CARBAMATE DERIVATIVES AND THEIR USE AS MUSCARINIC RECEPTOR ANTAGONISTS

The present invention relates to novel compounds of type 3-alkylphenylcarbamoyloxy-1-alkyl-1-azoniabicyclo[2.2.2] octane, acting as muscarinic receptor antagonists, to the preparation of such compounds, and to the use of the same in the prevention and treatment of diseases related with respiratory tract, digestive tract, and urinary system.

BACKGROUND OF THE ART

It is known that compounds having a muscarinic receptor antagonist effect induce bronchodilation, gastrointestinal motility inhibition, gastric acid secretion reduction, dry mouth, mydriasis, tachycardia, as well as urinary bladder contraction inhibition.

Between 1983 and 1993, continuous advances were produced in the knowledge of muscarinic receptor pharmacology. During this period, a total of five human genes codifying muscarinic receptor subtypes (m1, m2, m3, m4 and m5) were cloned and expressed, which encoded five functional receptors ($M_1$, $M_2$, $M_3$, $M_4$ and $M_5$).

The $M_1$ receptor is a postsynaptic neuronal receptor mainly located in brain and peripheral parasympathetic glands. In smooth cardiac muscle there is a major population of $M_2$ receptors. The $M_3$ receptor is predominantly located in glandular exocrine tissues such as salivary glands. The $M_4$ receptor is mainly present in cerebral cortex, striatum and some peripheral locations in specific species. The $M_5$ receptor has been described in the cerebral vessels. In the smooth muscle of intestinal tract, urinary bladder and bronchus, $M_2$ and $M_3$ receptors coexist. Nevertheless, functional information commonly accepted indicates that the $M_3$ receptor is the responsible for the contractile effect of the endogenous neurotransmitter in the last three tissues.

Few $M_3$ antagonists lacking $M_2$ affinity have been developed. The present invention contributes to fill this need by providing this kind of antagonists.

It seems interesting to obtain $M_3$ receptor selective antagonists to avoid the adverse effects due to blockade of other muscarinic receptors, mainly the cardiac effects due to $M_2$ receptor inhibition. At present, oxybutynin (Alza), trospium (Madaus) and tolterodine (Pharmacia), among others, are commercially available compounds showing reduced selectivity for $M_2$ and $M_3$ receptors. However, darifenacin (Pfizer), and solifenacin (Yamanouchi), both in clinical phase, exhibit $M_3$ antagonist activity with a reduced affinity towards $M_2$ receptor.

In contrast, tiotropium bromide (Böehringer Ingelheim) binds with similar affinity to muscarinic $M_3$ and $M_2$ receptors. However, it dissociates more slowly from $M_3$ than from $M_2$ receptors and subsequently has a long acting effect over $M_3$ receptor. In consequence, it may be considered as a functionally selective $M_3$ antagonist compound.

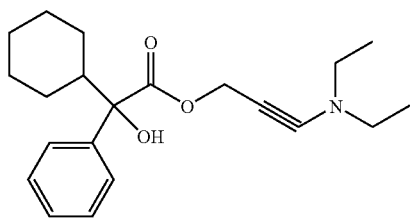

Oxybutynin

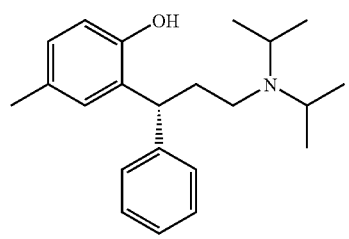

Tolterodine

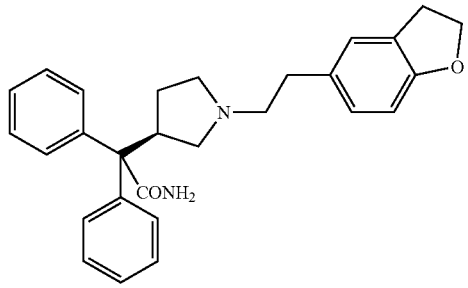

Darifenacin

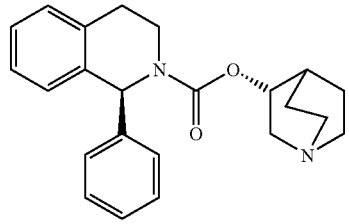

solifenacin

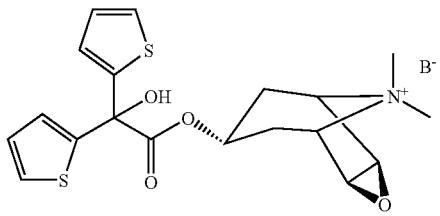

tiotropium

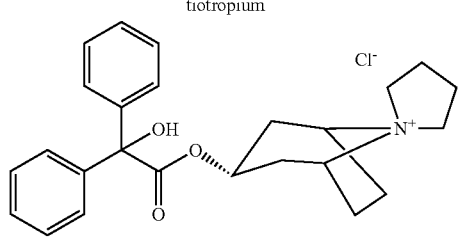

trospium

The following are some patent applications claiming compounds with carbamic structures as selective $M_3$ receptor antagonists: JP 04/95071, WO 9506635, EP 747355, EP 801067 and WO 0200652. All these documents describe carbamates different to those described in the present invention, and the later two describe the structurally nearest to the hereby claimed. In document WO 0104118 some alkylquinuclidinium esters are described as selective antagonist for $M_3$ receptors, but they are also different from the compounds claimed in the present invention.

The compounds claimed in the present invention may be used either alone or in association with other therapeutic agents selected from the group consisting of: calcium channel blockers, α-adrenoceptor antagonists, β$_2$-agonists, dopamine agonists, corticosteroids, phosphodiesterase 4 inhibitors, leukotriene D4 antagonists, endothelin antagonists, substance-P antagonists, antitussives, decongestants, histamine H$_1$ antagonists, 5-lipooxigenase inhibitors, VLA-4 antagonists and theophylline.

SUMMARY OF THE INVENTION

An aspect of the present invention relates to the provision of new alkylquinuclidinium carbamates of general formula (I)

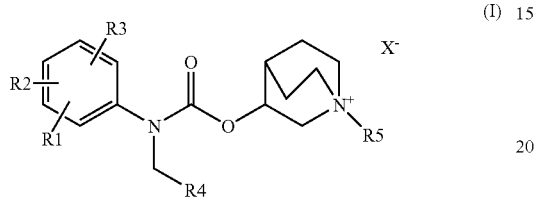

and prodrugs, individual isomers, racemic or non-racemic mixtures of isomers, pharmaceutically acceptable salts, polymorphs and solvates thereof, wherein R1, R2 and R3 are radicals independently selected from the group consisting of H, OH, NO$_2$, SH, CN, F, Cl, Br, I, COOH, CONH$_2$, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkoxyl optionally substituted with one or several F, and, (C$_1$-C$_4$)-alkyl optionally substituted with one or several F or OH; alternatively, either R1 and R2, or R2 and R3 may be forming a biradical selected from the group consisting of —CH$_2$—CH$_2$—CH$_2$—, and —CH$_2$—CH$_2$—CH$_2$—CH$_2$—;

R4 is a radical selected from the group consisting of:
  a) cyclopropyl, cyclobutyl, cyclopentyl, cyclohexyl, cyclohexenyl, norbornenyl, bicyclo[2.2.1]heptanyl, and 1-, 2-naphtyl, all of them optionally substituted with one or several substituents independently selected from the group consisting of OH, oxo (═O), SH, NO$_2$, CN, F, Cl, Br, I, CONH$_2$, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
  b) a C-linked radical of a five or six membered heterocyclic ring containing at least one heteroatom selected from the group consisting of O, S, and N, being this heterocyclic ring optionally substituted with one or several substituents independently selected from the group consisting of OH, oxo (═O), SH, NO$_2$, CN, F, Cl, Br, I, CONH$_2$, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
  c) a C-linked radical of a bicyclic ring system consisting of a phenyl ring fused to a five or six membered heterocyclic ring containing at least one heteroatom selected from the group consisting of O, S and N, being this bicyclic ring system optionally substituted with one or several substituents independently selected from the group consisting of OH, oxo (═O), SH, NO$_2$, CN, F, Cl, Br, I, CONH$_2$, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F; and
  d) phenyl optionally substituted with one or several substituents independently selected from the group consisting of OH, SH, NO$_2$, CN, F, Cl, Br, I, CONH$_2$, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;

R5 is a radical selected from the group consisting of:
  a) cyclopropyl, cyclobutyl, cyclopentyl, cyclohexyl, all of them optionally substituted with one or several substituents independently selected from the group consisting of OH, oxo (═O), SH, NO$_2$, CN, F, Cl, Br, I, CONH$_2$, NR7CO—(C$_1$-C$_4$)-alkyl, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
  b) (C$_5$-C$_{10}$)-alkyl;
  c) (C$_1$-C$_{10}$)-alkyl substituted with one or several radicals independently selected from the group consisting of R6, COR6, NH$_2$, NR6R7, CONR6R7, NR7COR6, OH, OR6, COOR6, OCOR6, SO$_2$R6, SH, SR6, SOR6, COSR6, SCOR6, CN, F, Cl, Br, NO$_2$, cyclopropyl, cyclobutyl, cyclopentyl, cyclohexyl, cyclohexenyl, norbornenyl, and bicyclo[2.2.1]heptanyl;

R6 is a radical selected from the group consisting of:
  a) (C$_1$-C$_5$)-alkyl, cyclopropyl, cyclobutyl, cyclopentyl, cyclohexyl, cyclohexenyl, norbornenyl, bicyclo[2.2.1]heptanyl, all of them optionally substituted with one or several substituents independently selected from the group consisting of OH, oxo (═O), SH, NO$_2$, CN, F, Cl, Br, I, CONH$_2$, NR7CO—(C$_1$-C$_4$)-alkyl, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
  b) phenyl optionally substituted with one or several substituents independently selected from the group consisting of OH, SH, NO$_2$, CN, F, Cl, Br, I, CONH$_2$, NR7CO—(C$_1$-C$_4$)-alkyl, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
  c) a C-linked radical of a five or six membered heterocyclic ring containing at least one heteroatom selected from the group consisting of O, S, and N, being this heterocyclic ring optionally substituted with one or several substituents independently selected from the group consisting of OH, oxo (═O), SH, NO$_2$, CN, F, Cl, Br, I, CONH$_2$, NR7CO—(C$_1$-C$_4$)-alkyl, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F; and
  d) a C-linked radical of a bicyclic ring system consisting of a phenyl ring fused to a five or six membered heterocyclic ring containing at least one heteroatom selected from the group consisting of O, S and N, being this bicyclic ring system optionally substituted with one or several substituents independently selected from the group consisting of OH, oxo (=O), SH, $NO_2$, CN, F, Cl, Br, I, $CONH_2$, COOH, NR7CO—($C_1$-$C_4$)-alkyl, ($C_1$-$C_4$)-alkoxycarbonyl, ($C_1$-$C_4$)-alkylsulfanyl, ($C_1$-$C_4$)-alkylsulfinyl, ($C_1$-$C_4$)-alkylsulfonyl, ($C_1$-$C_4$)-alkyl optionally substituted with one or several F or OH, and ($C_1$-$C_4$)-alkoxyl optionally substituted with one or several F;

R7 is a radical selected from the group consisting of H, phenoxycarbonyl, benzyloxycarbonyl, ($C_1$-$C_4$)-alkoxycarbonyl, ($C_1$-$C_4$)-alkylcarbonyl, ($C_1$-$C_4$)-alkylsulfonyl, and ($C_1$-$C_5$)-alkyl; and $X^-$ is a physiologically acceptable anion, such as chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

In a particular embodiment, R4 is 2-thiophene, 3-thiophene or phenyl, all of three cases optionally substituted with one or several substituents independently selected from the group consisting of OH, SH, $NO_2$, CN, F, Cl, Br, I, $CONH_2$, COOH, ($C_1$-$C_4$)-alkoxycarbonyl, ($C_1$-$C_4$)-alkylsulfanyl, ($C_1$-$C_4$)-alkylsulfinyl, ($C_1$-$C_4$)-alkylsulfonyl, ($C_1$-$C_4$)-alkyl optionally substituted with one or several F or OH, and ($C_1$-$C_4$)-alkoxyl optionally substituted with one or several F.

In another particular embodiment R5 is a ($C_1$-$C_5$)-alkyl substituted with one radical selected from the group consisting of R6, COR6, NR6R7, CONR6R7, NR7COR6, OR6, COOR6, OCOR6, SR6, SOR6, $SO_2R6$; and R6 is a radical selected from the group consisting of:
 a) phenyl optionally substituted with one or several substituents selected from the group consisting of OH, SH, CN, F, Cl, Br, I, $CONH_2$, COOH, ($C_1$-$C_4$)-alkoxycarbonyl, ($C_1$-$C_4$)alkylsulfanyl, ($C_1$-$C_4$)-alkylsulfinyl, ($C_1$-$C_4$)-alkylsulfonyl, ($C_1$-$C_4$)-alkyl optionally substituted with one or several F or OH, and ($C_1$-$C_4$)-alkoxyl optionally substituted with one or several F;
 b) a C-linked radical of a five or six membered heterocyclic ring containing at least one heteroatom selected from the group consisting of O, S, and N, being this heterocyclic ring optionally substituted with one or several substituents independently selected from the group consisting of OH, SH, $NO_2$, CN, F, Cl, Br, I, $CONH_2$, COOH, ($C_1$-$C_4$)-alkoxycarbonyl, ($C_1$-$C_4$)-alkylsulfanyl, ($C_1$-$C_4$)-alkylsulfinyl, ($C_1$-$C_4$)-alkylsulfonyl, ($C_1$-$C_4$)-alkyl optionally substituted with one or several F or OH, and ($C_1$-$C_4$)-alkoxyl optionally substituted with one or several F.

Another aspect of the present invention relates to new intermediate compound of formula (X)

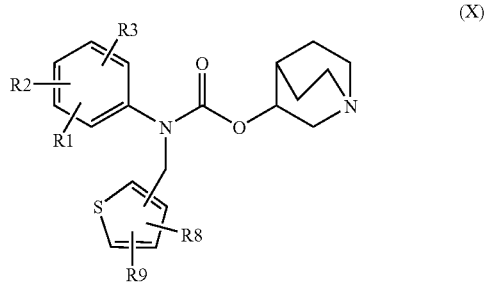

(X)

and prodrugs, individual isomers, racemic or non-racemic mixtures of isomers, pharmaceutically acceptable salts, polymorphs and solvates thereof,
for the preparation of a compound of formula (I) as defined in claim 1,
wherein R1, R2, R3, R8 and R9 are radicals independently selected from the group consisting of H, OH, $NO_2$, SH, CN, F, Cl, Br, I, $CONH_2$, COOH, ($C_1$-$C_4$)-alkoxycarbonyl, ($C_1$-$C_4$)-alkylsulfanyl, ($C_1$-$C_4$)-alkylsulfinyl, ($C_1$-$C_4$)-alkylsulfonyl, ($C_1$-$C_4$)-alkoxyl optionally substituted with one or several F, ($C_1$-$C_4$)-alkyl optionally substituted with one or several F or OH, except when R8 and R9 are H; alternatively, either R1 and R2, or R2 and R3 may be forming a biradical selected from the group consisting of —$CH_2$—$CH_2$—$CH_2$—, and —$CH_2$—$CH_2$—$CH_2$—$CH_2$—.

In still another particular embodiment of the present invention the configuration of the 3 position in the quinuclidine ring of all the preceding compounds is (R).

In cases where compounds of formula (I) have an asymmetric carbon, the racemic mixtures thereof may be resolved in their enantiomers by conventional methods, such as separation by column chromatography with chiral stationary phase or by fractioned crystallization of their diastereoisomeric salts. The later may be prepared by reaction with enantiomerically pure acids or bases. Chiral compounds of formula (I) may also be obtained by enantioselective synthesis through chiral precursors.

The present invention also relates to physiologically acceptable salts of carbamates of general structure (I). In this specification "physiologically acceptable salts" means salts that are pharmaceutically acceptable, and that possess the desired pharmacological activity of the parent compound.

Such salts include:
Acid addition salts formed with inorganic acids such as hydrochloric, hydrobromic, nitric, sulfuric, and phosphoric acids, as well as with organic acids such as acetic, benzenesulfonic, benzoic, camphorsulfonic, mandelic, methanesulfonic, oxalic, succinic, fumaric, tartaric and maleic acids.
Salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethylamine, and triethylamine. Acceptable inorganic bases include aluminium hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) of the same acid addition salt.

In this specification the terms 'alkyl' and 'alkoxyl' includes straight chained and branched structures.

Compounds of general structure (I) may be obtained from intermediates of general formula (IV), which may be prepared by three general methods (namely, A, B and C) represented in the scheme below.

Starting arylalkylamines (II) are commercially available, or may be obtained by known methods in the literature such as alkylation of anilines, reductive amination, or reduction of anilides.

According to Method A, acylation of the arylalkylamine (II) through a chloroformate (e.g. methylchloroformate, ethylchloroformate or 4-nitrophenylchloroformate) in an inert solvent [e.g. dimethylformamide (DMF), dichloromethane (DCM), 1,2-dichloroethane (1,2-DCE), tetrahydrofurane (THF) or toluene] is carried out first, at a temperature ranging from 0° C. to the reflux temperature of the solvent. In some cases, it is advisable to carry out the reaction using the corresponding chloroformate as solvent, or using a base such as a tertiary amine or potassium carbonate. Then, the alkoxylic moiety is introduced by a transesterification reaction between the carbamate intermediate (III) and 3-quinuclidol, using a base such as sodium metal, sodium hydride, or sodium methoxide. The reaction may be carried out at a temperature ranging from 0° C. to the reflux temperature of the solvent.

Method A

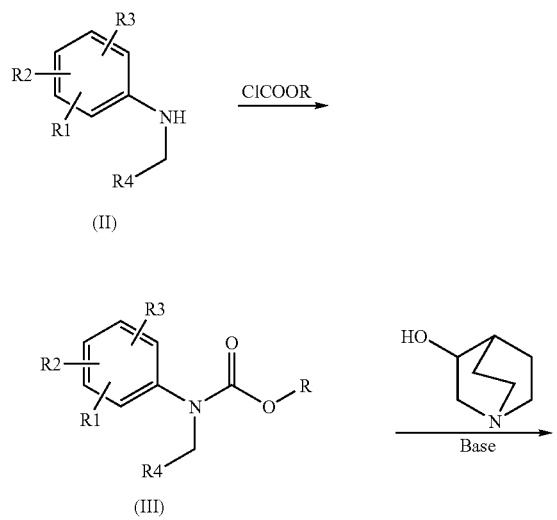

According to Method B, 3-quinuclidol is first reacted with a chloroformate (e.g. trichloromethylchloroformate) in an inert solvent (e.g. DMF, DCM, 1,2-DCE) at a temperature ranging from 0° C. to the reflux temperature of the solvent in order to obtain the corresponding hydrochloride of quinuclidol chloroformate. Then, arylalkylamine (II) is acylated with quinuclidol chloroformate. The reaction is carried out in an inert solvent (e.g. DMF, DCM, CHCl$_3$, 1,2-DCE) at a temperature ranging from 20° C. to the reflux temperature of the solvent.

Method B

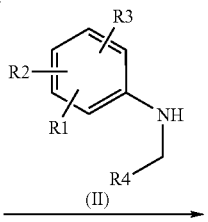

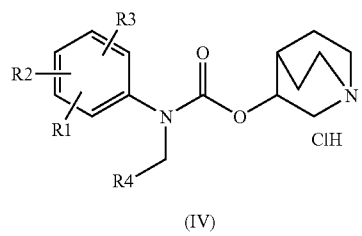

According to Method C, 3-quinuclidol is first reacted with a carbonyldiimidazole (DCI) in an inert solvent (e.g. DCM, 1,2-DCE) at room temperature in order to obtain the corresponding imidazole-1-carboxylic acid 1-azabicyclo[2.2.2]oct-3-yl ester. Then, arylalkylamine (II) is metalated in an inert solvent (e.g. THF) using BuLi and the ester was added at a temperature ranging from 0° C. to room temperature.

Method C

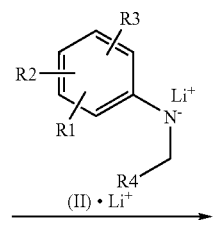

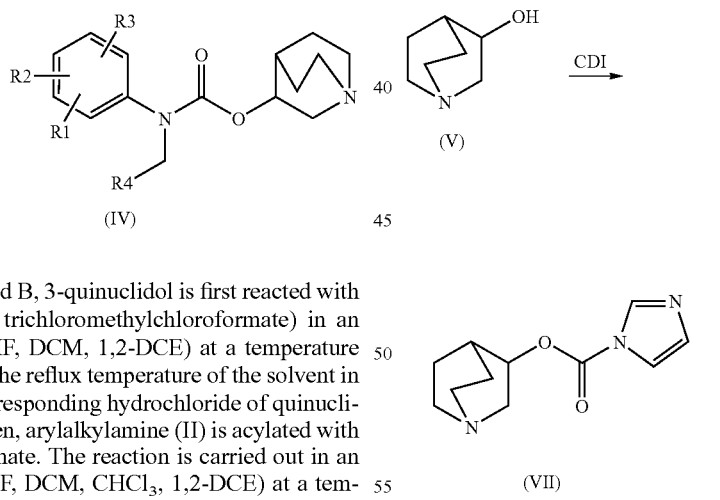

The quaternary ammonium salt of general formula (I), may be prepared by an N-alkylation reaction between an alkylating reagent (R5-X) and a compound of general formula (IV), using an inert solvent [e.g. DMF, DCM, CHCl₃, 1,2-DCE, CH₃CN (acetonitrile)] at a temperature ranging from 20° C. to the reflux temperature of the solvent.

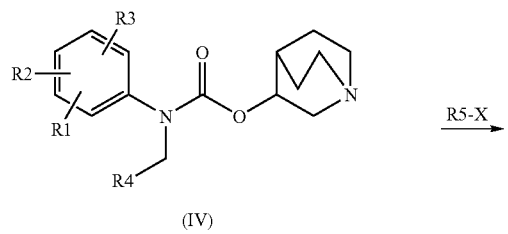

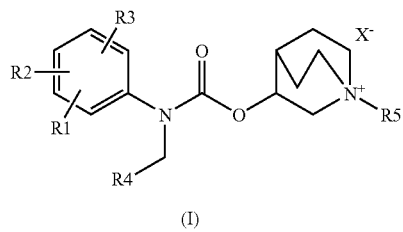

The R5-X compounds are either commercially available or may be prepared by known methods, such as those illustrated below.

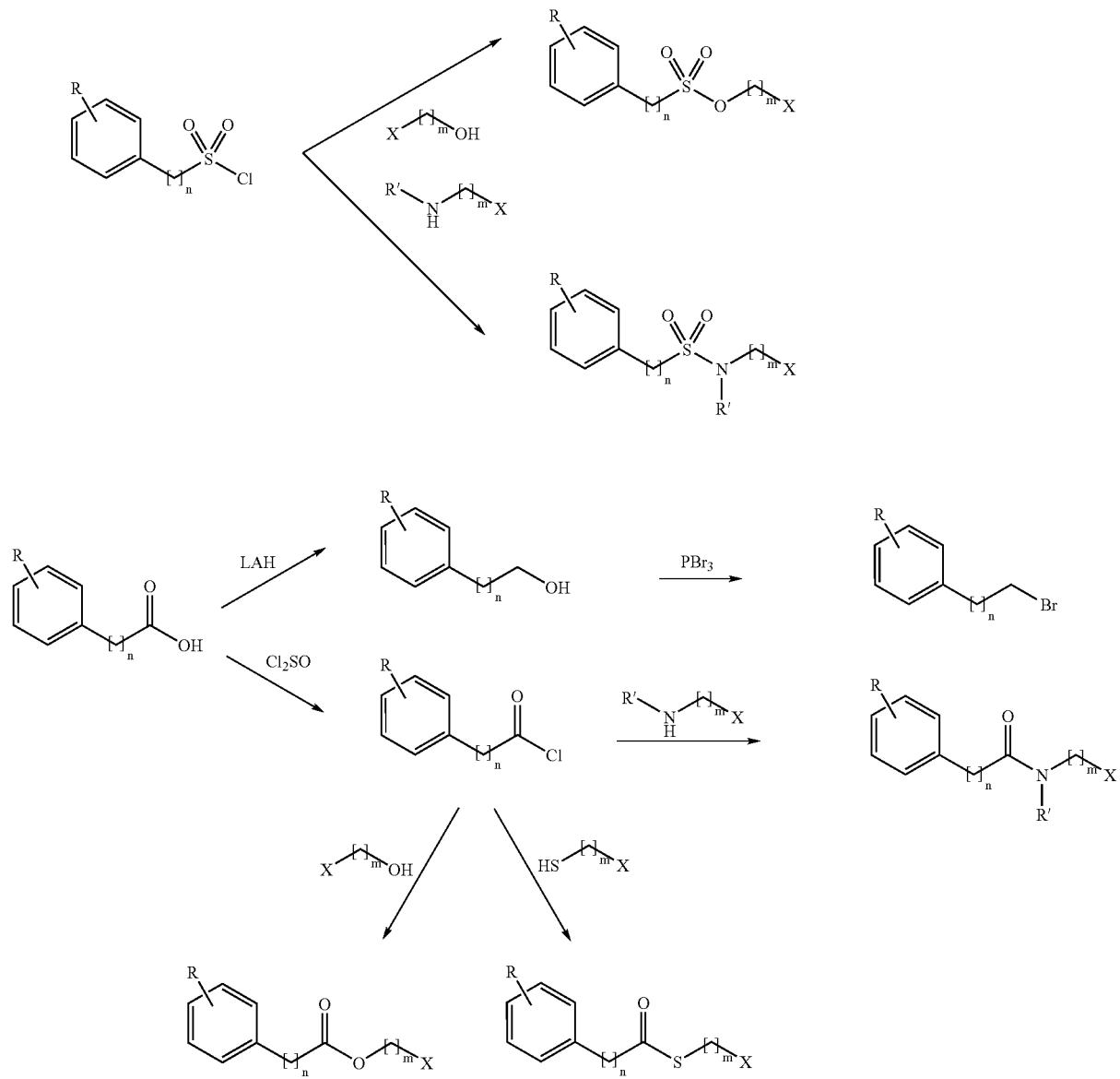

-continued
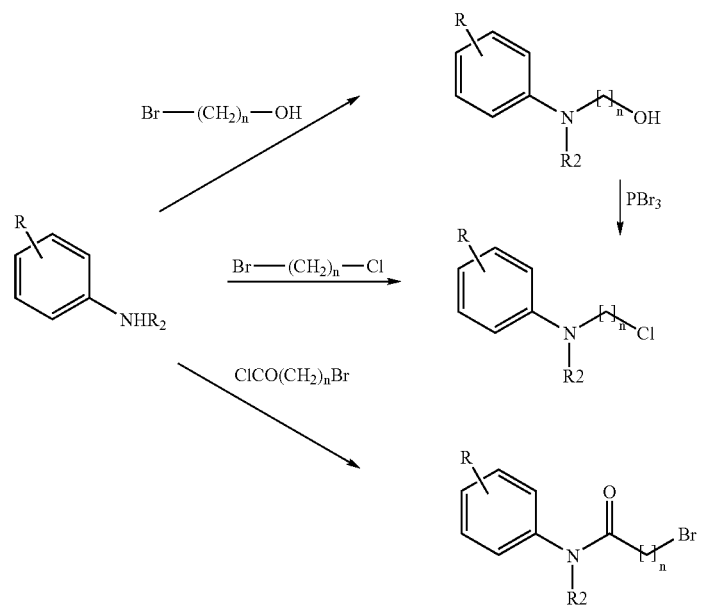
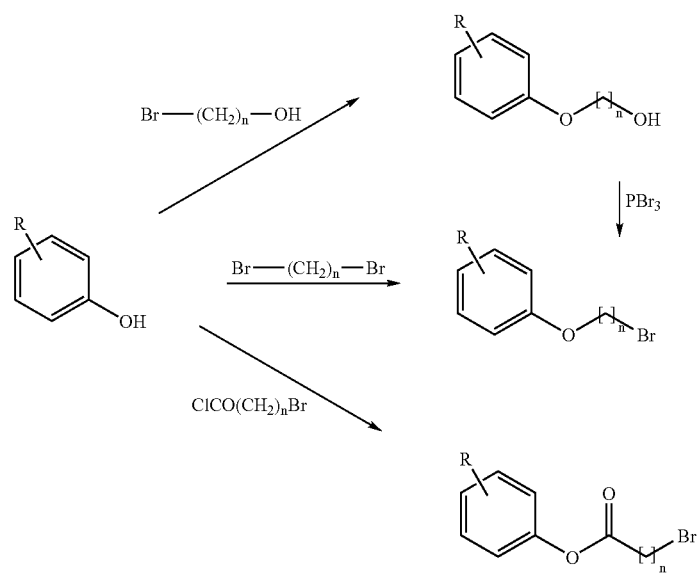

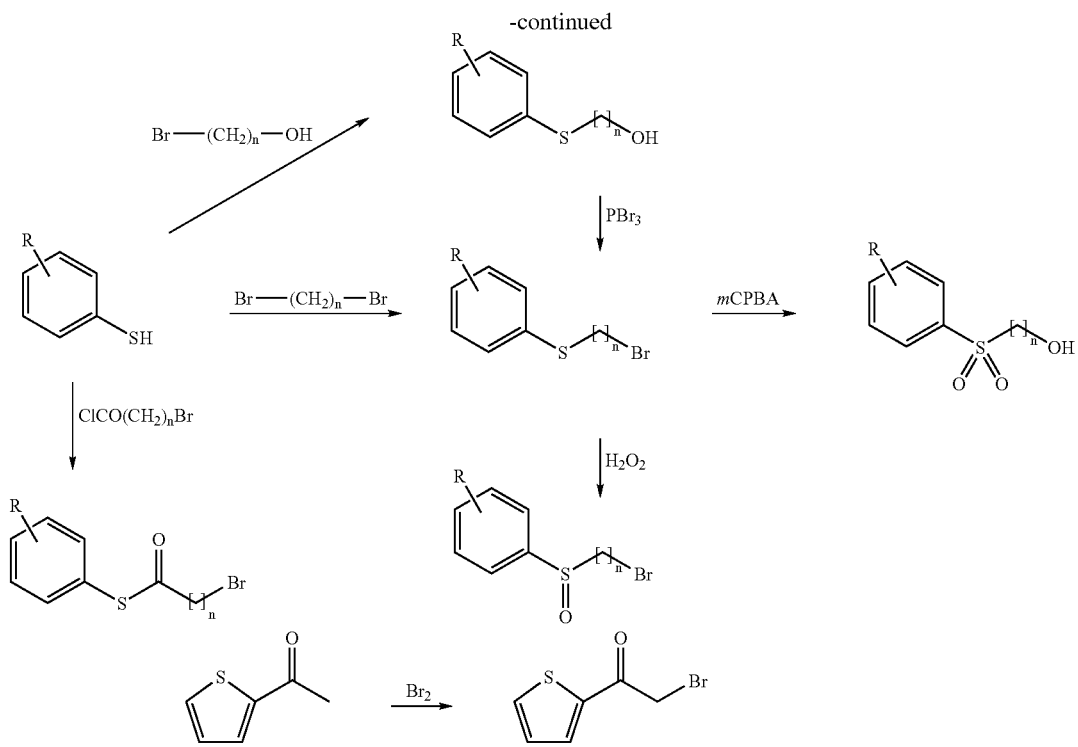

Additionally, when R5 is —CH$_2$—CHOH-A, wherein A is any radical except H, the quaternary amonium salt of general formula (I) may be prepared by alkylation between an epoxide and a compound of general formula (IV), in an inert solvent (e.g. DMF, DCM, CHCl$_3$, 1,2-DCE, CH$_3$CN) at a temperature ranging from 20° C. to the reflux temperature of the solvent.

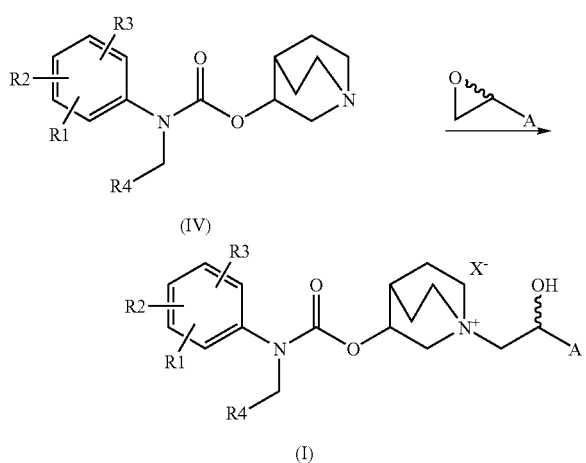

The compounds of the present invention are selective M$_3$ receptor antagonists versus M$_2$ receptor. For this reason they may be used for the treatment of urinary incontinence (particularly, the one caused by overactive bladder), irritable bowel syndrome, and respiratory disorders (particularly, chronic obstructive pulmonary disease, chronic bronchitis, asthma, emphysema, and rhinitis), as well as in ophthalmic interventions.

Thus, another aspect of the present invention is the use of carbamates of formula (I) for the preparation of medicaments for the treatment of the following diseases: urinary incontinence, particularly when it is caused by overactive bladder; irritable bowel syndrome; respiratory disorders, especially chronic obstructive pulmonary disease, chronic bronchitis, asthma, emphysema, and rhinitis. Furthermore, their use for the preparation of a medicament for ophthalmic interventions, is also forming part of this aspect of the invention.

Binding Test to Human M$_2$ and M$_3$ Muscarinic Receptors

The following tests show the M$_3$ antagonist activity of compounds of formula (I), as well as their selectivity towards the M$_2$ receptor. Some results obtained for cloned human muscarinic M$_2$ and M$_3$ receptors are listed, and the used methodology is described.

Membranes from CHO—K1 cells transfected with human M$_2$ or M$_3$ receptors were used. The summarised experimental procedure for both receptors was the following: cell membranes (15-20 µg) were incubated with [$^3$H]-NMS (0.3-0.5 nM) for 60 min at 25° C., in presence or absence of the antagonists. Incubation was carried out in 96 wells polystyrene microplates in a total incubation volume of 0.2 mL of PBS pH 7.4. Non specific binding was determined in parallel assays in presence of atropine (5 µM). Samples were filtered through type GF/C glass fibre, preincubated with PEI 0.3%. Filters were washed 3-4 times with 50 mM Tris-HCl, 0.9% NaCl, pH 7.4 at 4° C., and dried at 50° C. for 45 min. Filter bound radioactivity was quantified by liquid scintillation counting.

For the calculation of the inhibition constant (K$_i$), displacement curves were analysed by non-linear regression (GraphPad Prism). Dissociation constant (K$_d$) of [$^3$H]-NMS for each receptor was obtained through the saturation curves obtained in the same conditions as the experiments carried out with the corresponding antagonists. The results obtained, expressed as the mean of two independent experiments, each performed in duplicate, are shown in the table below. $M_2/M_3$ ratios greater than 1 indicates a $M_3$ selective activity.

|  | $M_3$ ($k_i$, nM) | $M_2/M_3$ (ratio) |
|---|---|---|
| OXYBUTYNIN | 2.04 | 3 |
| TOLTERODINE | 10.20 | 1 |
| DARIFENACIN | 2.97 | 56 |
| SOLIFENACIN | 8.30 | 10 |
| Int. 29 | 0.02 | 105 |
| Int. 32 | 0.15 | 23 |
| Ex. 11 | 0.34 | 80 |
| Ex. 50 | 0.06 | 345 |
| Ex. 69 | 0.02 | 32 |

EXAMPLES

The invention will be illustrated by the following non-limiting examples.

The structure of the different compounds was confirmed by $^1$H-NMR, recorded using a Varian GEMINI-200 or Gemini-300 MHz instruments and chemical shifts are expressed as ppm (δ) from the internal reference TMS. The nomenclature used in this document is based on AUTONOM (Automatic Nomenclature), a Beilstein Institute computerized system for the generation of IUPAC systematic nomenclature.

Intermediate 1: (R)-3-quinuclidyl chloroformate, hydrochloride

To a solution of 8.7 mL (74.8 mmol) of trichloromethyl chloroformate in 240 mL of dichloromethane, a solution of 4.75 g (37.4 mmol) of (R)-3-quinuclidol in 240 mL of dichloromethane was added dropwise at 0° C. under inert atmosphere and with continuous stirring. Then, the mixture was stirred at room temperature for 24 h, and the solvent was distilled off under reduced pressure to give 8.46 g (37.4 mmol) of a white solid corresponding to the title compound. IR (KBr, cm$^{-1}$): 3380, 2650-2500, 1776.

Intermediate 2: (R)-Imidazole-1-Carboxylic acid 1-azabicyclo[2.2.2]oct-3-yl ester To a suspension of 20.0 g (157 mmol) of (R)-3-quinuclidol in 400 mL of dichloromethane, 31.55 g (189 mmol) of DCI were added at room temperature. The yellow solution was stirred during 4 hrs under inert atmosphere. Then, 340 mL of water were added. The organic layer was dried over anhydrous sodium sulfate. The solvent was distilled off under reduced pressure. The obtained solid was crystallized with isopropyl acetate (IPAC)-heptane to give 23.5 g (68%) of the title compound. IR (KBr, cm$^{-1}$): 1746.

Intermediate 3: (R)-Benzylphenylcarbamic acid 1-azabicyclo[2.2.2]oct-3-yl ester hydrochloride Method A To a solution of 5.1 g (20 mmol) of benzylphenylcarbamic acid ethyl ester (Dannley, L. *J. Org. Chem.* 1957, 22, 268) and 7.63 g (60 mmol) of 3-quinuclidol in 120 mL of toluene, 800 mg (20 mmol) of sodium hydride (60% dispersion in oil) were added and the mixture was refluxed for three hours. During this time toluene was added to replace the distilled volume. The reaction crude was allowed to cool down, and was diluted with toluene (250 mL), washed with water and dried over anhydrous sodium sulfate. Then, the solvent was distilled off under reduced pressure. The obtained oil was treated at room temperature with hydrogen chloride saturated ethanol, the solvent was distilled off, and the obtained solid was broken up with a 1:1 ethyl acetate/diethyl ether mixture to give 230 mg (0.6 mmol) of a white solid corresponding to the title compound (m.p.: 54° C.).

Method B

To a suspension of 750 mg (2.58 mmol) of 3-quinuclidyl chloroformate hydrochloride in 20 mL of 1,2-DCE, a solution of 395 mg (2.15 mmol) of N-phenylbenzylamine in 5 mL of 1,2-DCE was added dropwise. Once completed the addition, the mixture was refluxed for three hours. The reaction crude was allowed to cool down and the solvent distilled off under reduced pressure. The residue was purified by column chromatography (SiO$_2$, eluent: CHCl$_3$-methanol 10:1) yielding 720 mg (1.95 mmol) of a hygroscopic foam corresponding to the title compound. IR (KBr, cm$^{-1}$): 3400-3200, 2700-2300, 1700 cm$^{-1}$. $^1$H-RMN (CDCl$_3$): 12.30 (s, 1H), 7.20-6.90 (m, 10H), 5.10 (m, 1H), 4.83 (m, 2H), 3.52 (m, 1H), 3.18 (m, 4H), 2.80 (m, 1H), 2.34 (s, 1H), 1.92 (m, 2H), 1.60 (m, 2H).

Method C

To a solution of 2.73 g (14.9 mmol) of N-phenylbenzylamine in 20 mL of THF, previously cooled at −10° C., 5.96 mL of n-BuLi (2.5 M) were added dropwise. At −10° C. 3.29 g (14.9 mmol) of intermediate 2 in 35 mL of THF were slowly added. The resulting mixture was stirred for 2 h and allowed to rise room temperature, then 35 mL of water was added. The solution was extracted with ethyl acetate, and the organic phase was dried over anhydrous sodium sulfate and the solvent was removed under reduced pressure. The residue was dissolved in EtOH/HCl and the solvent evaporated again. The new residue was purified by column chromatography (eluent: chloroform-methanol 10:1) yielding 1.53 g of an hygroscopic foam corresponding to the title compound. IR (KBr, cm$^{-1}$): 3400-3200, 2700-2300, 1700 cm$^{-1}$.

The following intermediates (4 to 15) were prepared using method B, described in the patent application WO 0200652:

Intermediate 4: (R)-Benzyl-m-tolylcarbamic acid 1-azabicyclo[2.2.2]oct-3-yl ester; hydrochloride.

Intermediate 5: (R)-Benzyl-(3-fluorophenyl)carbamic acid 1-azabicyclo[2.2.2]oct-3-yl ester; hydrochloride.

Intermediate 6: (R)-(4-Fluorobenzyl)phenylcarbamic acid 1-azabicyclo[2.2.2]oct-3-yl ester; hydrochloride.

Intermediate 7: (R)-(4-Fluorobenzyl)-m-tolylcarbamic acid 1-azabicyclo[2.2.2]oct-3-yl ester; hydrochloride.

Intermediate 8: (R)-(4-Fluorobenzyl)-(2-fluorophenyl)carbamic acid 1-azabicyclo[2.2.2]oct-3-yl ester; hydrochloride.

Intermediate 9: (R)-(4-Fluorobenzyl)-(3-fluorophenyl)carbamic acid 1-azabicyclo[2.2.2]oct-3-yl ester; hydrochloride.

Intermediate 10: (R)-(3,4-Difluorobenzyl)phenylcarbamic acid 1-azabicyclo[2.2.2]oct-3-yl ester; hydrochloride.

Intermediate 11: (R)-(3,4-Difluorobenzyl)-m-tolylcarbamic acid 1-azabicyclo[2.2.2]oct-3-yl ester; hydrochloride.

Intermediate 12: (R)-(3,4-Difluorobenzyl)-(2-fluorophenyl) carbamic acid 1-azabicyclo[2.2.2]oct-3-yl ester; hydrochloride.

Intermediate 13: (R)-(3,4-Difluorobenzyl)-(3-fluorophenyl) carbamic acid 1-azabicyclo[2.2.2]oct-3-yl ester; hydrochloride.

Intermediate 14: (R)-(2-Fluorophenyl)-(3,4,5-trifluorobenzyl)carbamic acid 1-azabicyclo[2.2.2]oct-3-yl ester; hydrochloride.

Intermediate 15: (R)-(3-Fluorophenyl)-(3,4,5-trifluorobenzyl)carbamic acid 1-azabicyclo[2.2.2]oct-3-yl ester; hydrochloride.

Intermediate 16: (R)-3-Cyclohexylmethylphenylcarbamoyloxy-1-azoniabicyclo[2.2.2]octane; hydrochloride The following new intermediates were prepared using any of the methods described above:

Intermediate 17:
(R)-Thiophen-2-ylmethyl-m-tolylcarbamic acid 1-azabicyclo[2.2.2]oct-3-yl ester $^1$H-NMR (CDCl$_3$): 7.25 (d, 1H), 7.22 (d, 1H), 7.06 (d, 1H), 6.94 (m, 1H), 6.91 (dd, 2H), 6.84 (dd, 1H), 4.95 (s, 2H), 4.88 (m, 1H), 3.32 (dd, 1H), 3.10-2.60 (m, 5H), 2.31 (s, 3H), 2.14 (m, 1H), 1.80-1.30 (m, 4H).

Intermediate 18: (R)-(2-Fluorophenyl)thiophen-2-ylmethylcarbamic acid 1-azabicyclo[2.2.2]oct-3-yl ester $^1$H-NMR (CDCl$_3$): 7.35-7.20 (m, 2H), 7.15-7.00 (m, 3H), 6.86 (m, 2H), 4.95 (s, 2H), 4.82 (m, 1H), 3.22 (m, 1H), 3.15-2.50 (m, 5H), 2.01 (m, 1H), 1.80-1.50 (m, 2H), 1.45-1.20 (m, 2H).

Intermediate 19: (R)-(3-Fluorophenyl)thiophen-2-ylmethylcarbamic acid 1-azabicyclo[2.2.2]oct-3-yl ester; hydrochloride $^1$H-NMR (CDCl$_3$): 7.35-7.20 (m, 2H), 7.15-7.00 (m, 3H), 6.86 (m, 2H), 4.95 (s, 2H), 4.82 (m, 1H), 3.22 (m, 1H), 3.15-2.50 (m, 5H), 2.01 (m, 1H), 1.80-1.50 (m, 2H), 1.45-1.20 (m, 2H).

Intermediate 20: (R)-(3-Methylthiophen-3-ylmethyl)phenylcarbamic acid 1-azabicyclo[2.2.2]oct-3-yl ester; hydrochloride $^1$H-NMR (CDCl$_3$): 11.69 (br, 1H), 7.29 (m, 3H), 7.17-6.90 (m, 3H), 6.71 (dd, 1H), 5.08 (m, 1H), 4.89 (s, 2H), 3.61 (m, 1H), 3.40-2.60 (m, 5H), 2.37 (m, 1H), 2.19-1.80 (m, 3H), 1.87 (s, 3H), 1.61 (m, 1H).

Intermediate 21: (R)-3-[(4-Bromothiophen-2-ylmethyl)phenylcarbamoyloxy]-1-azoniabicyclo[2.2.2]octane: hydrochloride $^1$H-NMR (CDCl$_3$): 7.42-7.30 (m, 3H), 7.15 (d, 1H), 7.08 (br, 2H), 6.79 (d, 1H), 5,30 (br, 1H), 5.04 (m, 1H), 4.90 (s, 2H), 3.55-3.40 (m, 1H), 3.20-2.95 (m, 4H), 2.80 (br, 1H), 2.32 (m, 1H), 2.00-1.65 (m, 2H), 1.59 (m, 2H).

Intermediate 22: (R)-(5-Methylthiophen-2-ylmethyl)phenylcarbamic acid 1-azabicyclo[2.2.2]oct-3-yl ester; hydrochloride $^1$H-NMR (CDCl$_3$): 12.20 (br, 1H), 7.40-7.28 (m, 3H), 7.16-6.90 (br, 2H), 6.59 (d, 1H), 6.53 (d, 1H), 5.09 (m, 1H), 4.85 (s, 2H), 3.53 (br, 1H), 3.35-3.00 (m, 4H), 2.82 (br, 1H), 2.45 (s, 3H), 2.39 (m, 1H), 2.10-1.55 (m, 4H).

Intermediate 23: (R)-(5-Chlorothiophen-2-ylmethyl)-(2-fluorophenyl)carbamic acid 1-azabicyclo[2.2.2]oct-3-yl ester; hydrochloride $^1$H-NMR (CDCl$_3$): 7.40-7.27 (m, 1H), 7.23-7.05 (m, 3H), 6.71 (d, 1H), 6.60 (d, 1H), 5.07 (m, 1H), 4.81 (s, 2H), 3.49 (m, 1H), 3.30-3.00 (m, 4H), 2.87 (m, 1H), 2.39 (m, 1H), 2.00-1.80 (m, 2H), 1.75-1.53 (m, 2H).

Intermediate 24: (R)-(5-Bromothiophen-2-ylmethyl)phenylcarbamic acid 1-azabicyclo[2.2.2]oct-3-yl ester; hydrochloride $^1$H-NMR (CDCl$_3$): 7.42-7.29 (m, 3H), 7.12-7.00 (m, 2H), 6.86 (d, 1H), 6.59 (d, 1H), 5.30 (br, 1H), 5.04 (m, 1H), 4.86 (s, 2H), 3.50-3.35 (m, 1H), 3.20-2.90 (m, 4H), 2.80 (br, 1H), 2.32 (m, 1H), 2.00-1.65 (m, 3H), 1.59 (m, 1H).

Intermediate 25: (R)-(5-Bromothiophen-2-ylmethyl)-m-tolylcarbamic acid 1-azabicyclo[2.2.2]oct-3-yl ester; hydrochloride $^1$H-NMR (CDCl$_3$): 7.21 (d, 1H), 7.11 (d, 1H), 6.95-6.80 (m, 2H), 6.86 (d, 1H), 6.60 (d, 1H), 5.03 (m, 1H), 4.84 (s, 2H), 3.50-3.35 (m, 1H), 3.20-2.95 (m, 4H), 2.80 (br, 1H), 2.34 (m, 1H), 2.34 (s, 3H), 2.00-1.60 (m, 4H).

Intermediate 26: (R)-(3-Fluorophenyl)thiophen-3-ylmethylcarbamic acid 1-azabicyclo[2.2.2]oct-3-yl ester; hydrochloride $^1$H-NMR (CDCl$_3$): 8.14 (br, 1H), 7.38-7.24 (m, 2H), 7.08 (d, 1H), 6.99-6.92 (m, 4H), 5.07 (m, 1H), 4.81 (s, 2H), 3.65 (ddd, 1H), 3.27-3.08 (m, 4H), 2.90 (q, 1H), 2.31 (m, 1H), 2.10-1.80 (m, 2H), 1.70-1.55 (m, 2H).

Intermediate 27: (R)-(2-Fluorophenyl)-(3-methylthiophen-2-ylmethyl)carbamic acid 1-azabicyclo[2.2.2]oct-3-yl ester; hydrochloride $^1$H-NMR (CDCl$_3$): 7.31 (m, 1H), 7.13 (d, 1H), 7.10-6.92 (m, 2H), 7.07 (d, 1H), 6.72 (d, 1H), 5.11 (m, 1H), 4.87 (m, 2H), 3.51 (m, 1H), 3.35-2.98 (m, 4H), 2.85 (m, 1H), 2.42 (m, 1H), 1.93 (s, 3H), 2.10-1.50 (m, 4H).

Intermediate 28: (R)-(2-Fluorophenyl)-(5-methylthiophen-2-ylmethyl)carbamic acid 1-azabicyclo[2.2.2]oct-3-yl ester; hydrochloride $^1$H-NMR (CDCl$_3$): 7.31 (m, 1H), 7.20-7.04 (m, 3H), 6.59 (d, 1H), 6.53 (dd, 1H), 5.09 (m, 1H), 4.80 (m, 2H), 3.53 (m, 1H), 3.37-3.00 (m, 4H), 2.86 (br, 1H), 2.45 (s, 3H), 2.44 (m, 1H), 2.10-1.55 (m, 4H).

Intermediate 29: (R)-(5-Chlorothiophen-2-ylmethyl)-(3-fluorophenyl)carbamic acid 1-azabicyclo[2.2.2]oct-3-yl ester; hydrochloride $^1$H-NMR (CDCl$_3$): 7.34 (td, 1H), 7.04 (td, 1H), 6.95-6.78 (m, 2H), 6.73 (d, 1H), 6.62 (d, 1H), 5.09 (m, 1H), 4.83 (s, 2H), 3.52 (m, 1H), 3.35-3.05 (m, 4H), 2.93 (br, 1H), 2.41 (m, 1H), 2.10-1.55 (m, 4H).

Intermediate 30: (R)-(5-Ethylthiophen-2-ylmethyl)-m-tolylcarbamic acid 1-azabicyclo[2.2.2]oct-3-yl ester; hydrochloride ¹H-NMR (CDCl₃): 7.40-7.28 (m, 3H), 7.15-7.02 (m, 2H), 6.61 (d, 1H), 6.57 (d, 1H), 5.12 (m, 1H), 4.87 (s, 2H), 3.55-3.35 (m, 1H), 3.20-2.95 (m, 4H), 2.80 (q, 2H), 2.80-2.70 (m, 1H), 2.35 (m, 1H), 2.00-1.55 (m, 4H), 1.28 (t, 3H).

Intermediate 31: (R)-Phenylthiophen-3-ylmethylcarbamic acid 1-azabicyclo[2.2.2]oct-3-yl ester; hydrochloride ¹H-NMR (CDCl₃): 7.35-7.24 (m, 4H), 7.12-6.92 (m, 2H), 7.03 (d, 1H), 6.96 (dd, 1H), 5.01 (m, 1H), 4.77 (s, 2H), 3.48 (ddd, 1H), 3.25-2.97 (m, 4H), 2.80 (m, 1H), 2.27 (m, 1H), 2.01-1.77 (m, 2H), 1.65-1.45 (m, 2H).

Intermediate 32: (R)-Thiophen-3-ylmethyl-m-tolylcarbamic acid 1-azabicyclo[2.2.2]oct-3-yl ester; hydrochloride ¹H-NMR (CDCl₃): 7.27 (dd, 1H), 7.18 (t, 1H), 7.06 (d, 1H), 7.04 (s, 1H), 6.97 (dd, 1H), 6.82 (br, 2H), 5.03 (m, 1H), 4.76 (s, 2H), 3.50 (m, 1H), 3.28-2.98 (m, 4H), 2.83 (m, 1H), 2.30 (s, 3H), 2.30 (m, 1H), 2.05-1.75 (m, 2H), 1.70-1.50 (m, 2H).

Intermediate 33: (R)-(2-Fluorophenyl)thiophen-3-ylmethylcarbamic acid 1-azabicyclo[2.2.2]oct-3-yl ester; hydrochloride ¹H-NMR (CDCl₃): 7.38-7.20 (m, 2H), 7.11 (d, 1H), 7.10-6.95 (m, 2H), 7.05 (s, 1H), 6.99 (dd, 1H), 5.02 (m, 1H), 4.78 (dd, 2H), 3.48 (m, 1H), 3.30-2.95 (m, 4H), 2.83 (m, 1H), 2.29 (m, 1H), 2.05-1.80 (m, 2H), 1.70-1.50 (m, 2H).

The following new intermediates were also prepared using any of the methods described above, and they have been identified by ¹H-NMR:

(R)-(3-Fluorophenyl)-(3-methylthiophen-2-ylmethyl)carbamic acid 1-azabicyclo[2.2.2]oct-3-yl ester; hydrochloride
(R)-3-(4-Bromothiophen-2-ylmethyl)-m-tolylcarbamic acid 1-azabicyclo[2.2.2]oct-3-yl ester; hydrochloride
(R)-(4-Bromothiophen-2-ylmethyl)-(2-fluorophenyl)carbamic acid 1-azabicyclo[2.2.2]oct-3-yl ester; hydrochloride
(R)-(4-Bromothiophen-2-ylmethyl)-(3-fluorophenyl)carbamic acid 1-azabicyclo[2.2.2]oct-3-yl ester; hydrochloride
(R)-(3-Fluorophenyl)-(5-methylthiophen-2-ylmethyl)carbamic acid 1-azabicyclo[2.2.2]oct-3-yl ester; hydrochloride
(R)-(5-Chlorothiophen-2-ylmethyl)phenylcarbamic acid 1-azabicyclo[2.2.2]oct-3-yl ester; hydrochloride
(R)-(5-Bromothiophen-2-ylmethyl)-(2-fluorophenyl)carbamic acid 1-azabicyclo[2.2.2]oct-3-yl ester; hydrochloride
(R)-(5-Bromothiophen-2-ylmethyl)-(3-fluorophenyl)carbamic acid 1-azabicyclo[2.2.2]oct-3-yl ester; hydrochloride
(R)-(5-Ethylthiophen-2-ylmethyl)phenylcarbamic acid 1-azabicyclo[2.2.2]oct-3-yl ester; hydrochloride
(R)-(5-Ethylthiophen-2-ylmethyl)-(2-fluorophenyl)carbamic acid 1-azabicyclo[2.2.2]oct-3-yl ester; hydrochloride
(R)-(5-Ethylthiophen-2-ylmethyl)-(3-fluorophenyl)carbamic acid 1-azabicyclo[2.2.2]oct-3-yl ester; hydrochloride

Example 1

(R)-3-(Benzylphenylcarbamoyloxy)-1-Cyclopropyl-1-azoniabicyclo[2.2.2]octane; bromide 200 mg (0.59 mmol) of Intermediate 3 and 0.47 mL of bromocyclopropane (0.59 mmol) were mixed in 5 mL of acetonitrile/chloroform (2:3). The resulting solution was refluxed for 12 hours. The solvent was evaporated and the residue purified by column chromatography [SiO₂, eluent: dichloromethane-methanol (20:1)] to yield 130 mg (47%) of an hygroscopic white solid, corresponding to the title compound. ¹H-NMR (CDCl₃): 7.27 (m, 10H), 4.87 (m, 2H), 4.80 (m, 1H), 3.18 (ddd, 1H), 3.01 (m, 1H), 2.80-2.50 (m, 5H), 2.23 (m, 1H), 1.98 (m, 2H), 1.65-1.18 (m, 6H).

The following compounds were synthesised according to Example 1:

Example 2

(R)-3-(Benzylphenylcarbamoyloxy)-1-(2-Chlorobenzyl)-1-azoniabicyclo[2.2.2]octane; chloride The yield was 131 mg (45%) as a yellow oil. IR (film, cm⁻¹): 1694. ¹H-NMR (CDCl₃): 7.60-7.16 (m, 14H), 5.03 (m, 1H), 4.92 (dd, 2H), 4.80 (s, 2H), 4.10 (m, 1H), 3.77 (m, 3H), 3.35 (m. 1H), 2.78 (m, 1H), 2.28 (m, 1H), 1.98 (m, 2H), 1.78 (m, 1H), 1.60 (m, 1H).

Example 3

(R)-3-(Benzylphenylcarbamoyloxy)-1-(5-methylsulfanyl-[1,3,4]thiadiazol-2-ylsulfanylmethyl)-1-azoniabicyclo[2.2.2]octane; chloride, The yield was 77 mg (53%) as white solid. ¹H-NMR (CDCl₃): 7.27-7.18 (m, 10H), 6.97 (t, 2H), 6.82 (dd, 2H), 5.12 (dd, 1H), 4.82 (m, 2H), 4.34 (s, 2H), 4.30-4.05 (m, 3H), 4.05-3.70 (m, 4H), 3.05 (dd, 1H), 2.33 (m, 1H), 2.10-1.50 (m, 4H).

Example 4

(R)-3-(Benzylphenylcarbamoyloxy)-1-ethoxycarbonylmethyl-1-azoniabicyclo[2.2.2]octane; bromide The yield was 60 mg (35%) as a oil. IR (film, cm⁻¹): 1743, 1701. ¹H-NMR (CDCl₃): 7.28 (m, 10H), 5.15-4.80 (m, 5H), 4.40-3.50 (m, 8H), 2.38 (m, 1H), 2.01 (m, 2H), 1.78 (m, 1H), 1.58 (m, 1H), 1.29 (t, 3H).

Example 5

(R)-3-(Benzyl-m-tolylcarbamoyloxy)-1-[2-(2,3-dihydrobenzofuran-5-yl)ethyl]-1-azoniabicyclo[2.2.2]octane; bromide The yield was 120 mg (25%) as white solid. IR (film, cm⁻¹): 1694. ¹H-NMR (CDCl₃): 7.30-6.80 (m, 11H), 6.62 (d, 1H), 5.16 (m, 1H), 4.77 (m, 2H), 4.48 (t, 2H), 4.21 (m, 1H), 3.90-3.40 (m, 6H), 3.09 (t, 2H), 2.88 (m, 3H), 2.29 (s, 3H), 2.01-1.40 (m, 5H).

Example 6

(R)-3-[Benzyl-(3-fluorophenyl)carbamoyloxy]-1-[2-(2,3-dihydrobenzofuran-5-yl)ethyl]-1-azoniabicyclo[2.2.2]octane; bromide The yield was 51 mg (16%) as white solid. IR (film, cm$^{-1}$): 1705. $^1$H-NMR (CDCl$_3$): 7.30-6.90 (m, 10H), 6.80 (d, 1H), 6.68 (d, 1H), 5.17 (m, 1H), 4.90 (m, 2H), 4.52 (t, 2H), 4.16 (m, 1H), 3.90-3.60 (m, 5H), 3.41 (m, 1H), 3.13 (t, 2H), 2.88 (m, 3H), 2.21-1.60 (m, 5H).

Example 7

(R)-3-[(4-Fluorobenzyl)phenylcarbamoyloxy]-1-(2-m-tolylethyl)-1-azoniabicyclo[2.2.2]octane; bromide The yield was 110 mg (42%) as a yellow solid. $^1$H-NMR (CDCl$_3$): 7.40-7.00 (m, 10H), 7.09 (s, 1H), 6.98 (t, 2H), 5.09 (m, 1H), 4.78 (m, 2H), 4.13 (m, 1H), 4.00-3.60 (m, 5H), 3.30 (br, 1H), 2.95 (br, 1H), 2.93 (t, 2H), 2.33 (m, 1H), 2.30 (s, 3H), 2.10-1.70 (m, 3H), 1.61 (m, 1H).

Example 8

(R)-1-[2-(4-Ethoxyphenyl)ethyl]-3-[(4-fluorobenzyl)phenylcarbamoyloxy]-1-azoniabicyclo[2.2.2]octane; bromide The yield was 106 mg (38%) as white solid. $^1$H-NMR (CDCl$_3$): 7.40-6.95 (m, 11H), 6.79 (d, 2H), 5.06 (m, 1H), 4.78 (m, 2H), 4.15-3.60 (m, 6H), 3.95 (q, 2H), 3.35 (br, 1H), 3.05 (br, 1H), 2.93 (t, 2H), 2.32 (m, 1H), 2.10-1.70 (m, 4H), 1.38 (t, 3H).

Example 9

(R)-3-[(4-Fluorobenzyl)phenylcarbamoyloxy]-1-[2-(4-nitrophenyl)ethyl]-1-azoniabicyclo[2.2.2]octane; bromide The yield was 72 mg (26%) as yellow solid. $^1$H-NMR (CDCl$_3$): 8.04 (d, 2H), 7.59 (d, 2H), 7.40-7.03 (m, 7H), 6.98 (t, 2H), 5.11 (m, 1H), 4.79 (m, 2H), 4.25 (m, 1H), 4.05 (m, 1H), 3.95-3.70 (m, 4H), 3.55 (br, 1H), 3.16 (t, 2H), 3.05 (br, 1H), 2.93 (t, 2H), 2.32 (m, 1H), 2.10-1.50 (m, 4H).

Example 10

(R)-1-[2-(2,4-Difluorophenylsulfanyl)ethyl]-3-[(4-fluorobenzyl)phenylcarbamoyloxy]-1-azoniabicyclo[2.2.2]octane; bromide The yield was 182 mg (64%) as yellow solid. $^1$H-NMR (CDCl$_3$): 7.61 (ddd, 1H), 7.40-7.17 (m, 6H), 7.09 (m, 1H), 7.00-6.88 (m, 2H), 6.97 (t, 1H), 6.82 (dd, 1H), 5.11 (m, 1H), 4.78 (s, 2H), 4.23 (ddd, 1H), 4.00-3.50 (m, 5H), 3.45-3.20 (m, 3H), 2.93 (br, 1H), 2.32 (m, 1H), 2.10-1.80 (m, 3H) 1.60 (m, 1H).

Example 11

(R)-3-[(4-Fluorobenzyl)phenylcarbamoyloxy]-1-(3-phenoxypropyl)-1-azoniabicyclo[2.2.2]octane; bromide The yield was 32 mg (10%) as white solid. IR (film, cm$^{-1}$): 1703. $^1$H-NMR (CDCl$_3$): 7.40-6.80 (m, 12H), 6.85 (d, 2H), 5.13 (m, 1H), 4.88 (m, 2H), 4.18 (m, 1H), 4.05 (t, 2H), 3.90-3.60 (m, 4H), 3.47 (m, 1H), 3.23 (m, 1H), 2.80 (m, 1H), 2.40-1.80 (m, 7H).

Example 12

(R)-1-Cyclobutylmethyl-3-[(4-fluorobenzyl)-m-tolylcarbamoyloxy]-1-azoniabicyclo[2.2.2]octane; bromide The yield was 132 mg (63%) as an oil. $^1$H-NMR (CDCl$_3$): 7.25-7.17 (m, 3H), 7.06 (d, 2H), 7.00 (d, 2H), 6.88 (br, 1H), 5.09 (m, 1H), 4.78 (m, 2H), 4.10-3.80 (m, 3H), 3.56 (d, 2H), 3.55 (m, 1H), 3.05 (br, 1H), 2.75 (br, 1H), 2.35 (m, 1H), 2.32 (s, 3H), 2.10-0.90 (m, 11H).

Example 13

(R)-1-[2-(3,4-Dimethoxyphenyl)ethyl]-3-[(4-fluorobenzyl)-(2-fluorophenyl)carbamoyloxy]-1-azoniabicyclo[2.2.2]octane; bromide The yield was 190 mg (60%) as a white solid. $^1$H-NMR (CDCl$_3$): 7.35-6.92 (m, 10H), 6.76 (s, 2H), 5.08 (m, 1H), 4.78 (s, 2H), 4.25-3.60 (m, 6H), 3.95 (s, 3H), 3.82 (s, 3H), 3.26 (m, 1H), 2.97 (m, 3H), 2.30 (m, 1H), 2.10-1.50 (m, 4H).

Example 14

(R)-3-[(4-Fluorobenzyl)-(2-fluorophenyl)carbamoyloxy]-1-[2-(4-methoxyphenyl)-2-oxoethyl]-1-azoniabicyclo[2.2.2]octane; bromide The yield was 47 mg (19%) as a yellow solid. $^1$H-NMR (CDCl$_3$): 8.11 (d, 2H), 7.30-6.87 (m, 10H), 5.80-5.50 (m, 2H), 5.15 (m, 1H), 4.78 (m, 2H), 4.53 (m, 1H), 4.35-3.90 (m, 3H), 3.82 (s, 3H), 3.55 (m, 1H), 2.86 (m, 1H), 2.45-1.80 (m, 4H), 1.60 (m, 1H).

Example 15

(R)-3-[(4-Fluorobenzyl)-(2-fluorophenyl)carbamoyloxy]-1-[2-oxo-2-(1H-pyrrol-2-yl)ethyl]-1-azoniabicyclo[2.2.2]octane; bromide The yield was 90 mg (55%) as a brown solid. $^1$H-NMR (CDCl$_3$): 7.35-7.00 (m, 9H), 6.97 (t, 2H), 5.30 (m, 2H), 5.11 (m, 1H), 4.76 (m, 2H), 4.43 (m, 1H), 4.10-3.80 (m, 4H), 3.49 (m, 1H), 3.20 (br, 1H), 2.33 (m, 1H), 2.10-1.55 (m, 4H).

Example 16

(R)-3-[(4-Fluorobenzyl)-(2-fluorophenyl)carbamoyloxy]-1-(2-oxo-2-thiophen-2-ylethyl)-1-azoniabicyclo[2.2.2]octane; bromide The yield was 101 mg (60%) as a yellow solid. $^1$H-NMR (CDCl$_3$): 8.39 (d, 2H), 7.73 (d, 1H), 7.30-7.18 (m, 3H), 7.13

(s, 1H), 7.10-7.05 (m, 3H), 6.97 (t, 2H), 5.71 (dd, 2H), 5.15 (m, 1H), 4.78 (dd, 2H), 4.51 (m, 1H), 4.35-3.90 (m, 4H), 3.56 (m, 1H), 2.35 (m, 1H), 2.45-1.55 (m, 4H).

Example 17

(R)-3-[(4-Fluorobenzyl)-(2-fluorophenyl)carbamoyloxy]-1-(3-methoxyphenoxycarbonylmethyl)-1-azoniabicyclo[2.2.2]octane; bromide The yield was 43 mg (24%) as a yellow solid. $^1$H-NMR (CDCl$_3$): 7.35-7.16 (m, 7H), 7.13-7.00 (m, 3H), 6.97 (t, 2H), 5.21-4.90 (m, 3H), 4.85 (d, 1H), 4.76 (d, 1H), 4.41 (m, 1H), 4.25-3.60 (m, 4H), 3.76 (s, 3H), 3.53 (m, 1H), 2.35 (m, 1H), 2.20-1.70 (m, 3H), 1.60 (m, 1H).

Example 18

(R)-1-Cyclopentylcarbamoylmethyl-3-[(4-fluorobenzyl)-(2-fluorophenyl)carbamoyloxy]-1-azoniabicyclo[2.2.2]octane; bromide The yield was 100 mg (39%) as a brown solid. $^1$H-NMR (CDCl$_3$): 8.78 (m, 1H), 7.35-7.00 (m, 6H), 6.97 (t, 2H), 5.11 (m, 1H), 4.78 (s, 2H), 4.61 (d, 1H), 4.30-3.85 (m, 4H), 4.23 (d, 1H), 3.80-3.60 (m, 3H), 3.21 (m, 1H), 2.37 (m, 1H), 2.10-1.40 (m, 12H).

Example 19

(R)-3-[(4-Fluorobenzyl)-(2-fluorophenyl)carbamoyloxy]-1-[(2-fluorophenylcarbamoyl)methyl]-1-azoniabicyclo[2.2.2]octane; bromide The yield was 93 mg (60%) as a brown solid. $^1$H-NMR (CDCl$_3$): 10.23 (br, 1H), 7.73 (td, 1H), 7.40-6.98 (m, 9H), 6.94 (t, 2H), 5.15 (m, 1H), 5.01 (d, 1H), 4.79 (s, 2H), 4.72 (d, 1H), 4.45 (m, 1H), 4.30-3.70 (m, 4H), 3.39 (m, 1H), 2.38 (m, 1H), 2.10-1.60 (m, 4H).

Example 20

(R)-1-[2-(4-acetylaminophenylsulfanyl)ethyl]-3-[(4-fluorobenzyl)-(2-fluorophenyl)carbamoyloxy]-1-azoniabicyclo[2.2.2]octane; bromide The yield was 30 mg (9%) as a yellow solid. $^1$H-NMR (CDCl$_3$): 9.52 (s, 1H), 7.63 (d, 2H), 7.40-6.94 (m, 9H), 5.10 (m, 1H), 4.73 (s, 2H), 4.30-4.00 (m, 2H), 3.95-3.60 (m, 4H), 3.40-3.20 (m, 3H), 2.90 (m, 1H), 2.35 (m, 1H), 2.19 (s, 3H), 2.10-1.50 (m, 4H).

Example 21

(R)-1-[2-(2,3-Dimethylphenylsulfanyl)ethyl]-3-[(4-fluorobenzyl)-(2-fluorophenyl)carbamoyloxy]-1-azoniabicyclo[2.2.2]octane; bromide The yield was 94 mg (59%) as a yellow solid. $^1$H-NMR (CDCl$_3$): 7.35-7.00 (m, 9H), 6.96 (t, 2H), 5.11 (m, 1H), 4.76 (s, 2H), 4.25-3.90 (m, 3H), 3.85-3.40 (m, 3H), 3.40-3.10 (m, 3H), 2.86 (m, 1H), 2.35 (m, 3H), 2.33 (m, 1H), 2.30 (s, 3H), 2.20-1.50 (m, 4H).

Example 22

(R)-3-[(4-Fluorobenzyl)-(2-fluorophenyl)carbamoyloxy]-1-[2-(1-methyl-1H-imidazol-2-ylsulfanyl)ethyl]-1-azoniabicyclo[2.2.2]octane; chloride The yield was 79 mg (49%) as a brown oil. $^1$H-NMR (CDCl$_3$): 7.67 (d, 1H), 7.32-7.05 (m, 6H), 6.97 (t, 2H), 6.73 (d, 1H), 5.13 (m, 1H), 4.77 (s, 2H), 4.65 (m, 2H), 4.40-4.10 (m, 2H), 4.10-3.60 (m, 4H), 3.56 (s, 3H), 3.12 (m, 1H), 2.85 (m, 1H), 2.31 (m, 1H), 2.20-1.70 (m, 3H), 1.60 (m, 1H).

Example 23

(3R,SS) and (3R,SR)-3-[(4-Fluorobenzyl)-(2-fluorophenyl)carbamoyloxy]-1-[2-(2-methoxybenzenesulfinyl)ethyl]-1-azoniabicyclo[2.2.2]octane; chloride The yield was 72 mg (47%) as a white solid. $^1$H-NMR (CDCl$_3$): 7.62 (d, 1H), 7.52 (t, 1H), 7.35-7.00 (m, 8H), 6.96 (t, 2H), 5.12 (m, 1H), 4.76 (s, 2H), 4.20 (m, 1H), 4.10-3.80 (m, 2H), 3.94 (s, 3H), 3.75-3.50 (m, 4H), 3.41 (m, 1H), 3.17 (m, 1H), 2.85 (m, 1H), 2.33 (m, 1H), 2.20-1.80 (m, 3H), 1.59 (m, 1H).

Example 24

(R)-3-[(4-Fluorobenzyl)-(2-fluorophenyl)carbamoyloxy]-1-(methoxyphenylsulfanylcarbonylmethyl)-1-azoniabicyclo[2.2.2]octane; bromide The yield was 66 mg (31%) as a yellow solid. $^1$H-NMR (CDCl$_3$): 7.35-7.00 (m, 10H), 6.97 (t, 2H), 5.25-5.05 (m, 3H), 4.77 (dd, 2H), 4.50-3.80 (m, 5H), 3.76 (s, 3H), 3.50 (m, 1H), 2.32 (m, 1H), 2.10-1.50 (m, 4H).

Example 25

(R)-1-(2-Benzoyloxyethyl)-3-[(4-fluorobenzyl)-(2-fluorophenyl)carbamoyloxy]-1-azoniabicyclo[2.2.2]octane; bromide The yield was 52 mg (30%) as a white solid. $^1$H-NMR (CDCl$_3$): 8.02 (d, 2H), 7.62 (t, 1H), 7.48 (t, 2H), 7.30-6.85 (m, 8H), 5.12 (m, 1H), 4.80-4.65 (m, 4H), 4.45-3.80 (m, 6H), 3.59 (m, 1H), 3.20 (m, 1H), 2.37 (m, 1H), 2.10-1.60 (m, 4H).

Example 26

(R)-1-(2-Benzoylaminoethyl)-3-[(4-fluorobenzyl)-(2-fluorophenyl)carbamoyloxy]-1-azoniabicyclo[2.2.2]octane; chloride The yield was 56 mg (39%) as a brownish solid. $^1$H-NMR (CDCl$_3$): 9.38 (s, 1H), 8.06 (d, 2H), 7.55-7.30 (m, 4H), 7.30-7.00 (m, 5H), 6.94 (t, 2H), 5.09 (m, 1H), 4.74 (s, 2H), 4.10 (m, 1H), 4.05-3.60 (m, 5H), 3.32 (m, 1H), 2.95 (m, 1H), 2.40 (m, 2H), 2.27 (m, 1H), 2.10-1.70 (m, 3H), 1.59 (m, 1H).

Example 27

(R)-1-[2-(1,3-Dioxo-1,3-dihydroisoindol-2-yl)ethyl]-3-[(4-fluorobenzyl)-(2-fluorophenyl)carbamoyloxy]-1-azoniabicyclo[2.2.2]octane; bromide The yield was 56 mg (39%) as a brownish solid. $^1$H-NMR (CDCl$_3$): 7.82-7.70 (m, 4H), 7.35-7.00 (m, 6H), 6.96 (t, 2H), 5.13 (m, 1H), 4.77 (s, 2H), 4.35-3.80 (m, 8H), 3.40-2.95 (m, 2H), 2.35 (m, 1H), 2.10-1.70 (m, 3H), 1.59 (m, 1H).

Example 28

(R)-1-(2-Benzenesulfonylaminoethyl)-3-[(4-fluorobenzyl)-(2-fluorophenyl)carbamoyloxy]-1-azoniabicyclo[2.2.2]octane; bromide The yield was 64 mg (39%) as a brownish solid. $^1$H-NMR (CDCl$_3$): 7.90-7.76 (m, 3H), 7.47 (dd, 2H), 7.45-7.30 (m, 1H), 7.35 (dd, 1H), 7.25-7.00 (m, 4H), 6.93 (t, 2H), 5.03 (m, 1H), 4.75 (dd, 2H), 4.00 (m, 1H), 3.80-3.50 (m, 6H), 3.40-3.00 (m, 3H), 2.37 (m, 1H), 2.10-1.60 (m, 4H).

Example 29

(R)-1-[3-(2-Cyanophenoxy)propyl]-3-[(4-fluorobenzyl)-(2-fluorophenyl)carbamoyloxy]-1-azoniabicyclo[2.2.2]octane; chloride The yield was 92 mg (55%) as a yellow solid. $^1$H-NMR (CDCl$_3$): 7.54 (m, 2H), 7.35-6.90 (m, 10H), 5.17 (m, 1H), 4.78 (s, 2H), 4.35-3.80 (m, 8H), 3.31 (m, 1H), 3.01 (m, 1H), 2.45-1.80 (m, 6H), 1.65 (m, 1H).

Example 30

(R)-3-[(4-Fluorobenzyl)-(2-fluorophenyl)carbamoyloxy]-1-[3-(3-nitrophenoxy)propyl]-1-azoniabicyclo[2.2.2]octane; chloride The yield was 250 mg (47%) as a white solid. $^1$H-NMR (CDCl$_3$): 7.83 (ddd, 1H), 7.67 (t, 1H), 7.44 (t, 1H), 7.33-7.00 (m, 7H), 6.96 (t, 2H), 5.16 (m, 1H), 4.78 (s, 2H), 4.18 (t, 2H), 4.15-3.60 (m, 6H), 3.25 (m, 1H), 2.97 (m, 1H), 2.35-1.80 (m, 6H), 1.63 (m, 1H).

Example 31

(R)-3-[(4-Fluorobenzyl)-(2-fluorophenyl)carbamoyloxy]-1-[3-(4-methylpyrimidin-2-yloxy)propyl]-1-azoniabicyclo[2.2.2]octane; bromide The yield was 25 mg (11%) as a orange solid. $^1$H-NMR (CDCl$_3$): 7.50-6.90 (m, 10H), 5.16 (m, 1H), 4.78 (s, 2H), 4.15 (m, 1H), 4.15-3.40 (m, 7H), 3.22 (m, 1H), 2.92 (m, 1H), 2.40-1.80 (m, 9H), 1.63 (m, 1H).

Example 32

(R)-3-[(4-Fluorobenzyl)-(2-fluorophenyl)carbamoyloxy]-1-[3-(pyridin-2-ylsulfanyl)propyl]-1-azoniabicyclo[2.2.2]octane; bromide The yield was 24 mg (11%) as a red oil. $^1$H-NMR (CDCl$_3$): 8.41 (ddd, 1H), 7.51 (td, 1H), 7.35-6.90 (m, 10H), 5.13 (m, 1H), 4.76 (s, 2H), 4.20-3.55 (m, 6H), 3.23 (t, 2H), 3.15 (m, 1H), 2.85 (m, 1H), 2.34 (m, 1H), 2.20-1.60 (m, 6H).

Example 33

(R)-1-[3-(Benzooxazol-2-ylsulfanyl)propyl]-3-[(4-fluorobenzyl)-(2-fluorophenyl)carbamoyloxy]-1-azoniabicyclo[2.2.2]octane; chloride The yield was 80 mg (35%) as a orange solid. $^1$H-NMR (CDCl$_3$): 7.35-7.00 (m, 10H), 6.96 (t, 2H), 5.17 (m, 1H), 4.77 (s, 2H), 4.20 (m, 1H), 4.00-3.55 (m, 5H), 3.69 (t, 2H), 3.15 (m, 1H), 2.85 (m, 1H), 2.57 (m, 2H), 2.40-1.80 (m, 4H), 1.57 (m, 1H).

Example 34

(R)-1-[3-(2-Fluorobenzenesulfonyl)propyl]-3-[(4-fluorobenzyl)-(2-fluorophenyl)carbamoyloxy]-1-azoniabicyclo[2.2.2]octane; chloride The yield was 81 mg (45%) as a brown solid. $^1$H-NMR (CDCl$_3$): 7.89 (td, 1H), 7.68 (tdd, 1H), 7.34 (td, 1H), 7.30-7.00 (m, 7H), 6.96 (t, 2H), 5.12 (m, 1H), 4.76 (s, 2H), 4.10 (m, 1H), 4.00-3.60 (m, 5H), 3.48 (t, 2H), 3.21 (m, 1H), 2.93 (m, 1H), 2.50-1.70 (m, 6H), 1.60 (m, 1H).

Example 35

(R)-1-{3-[Acetyl-(3-Chlorophenyl)amino]propyl}-3-[(4-fluorobenzyl)-(2-fluorophenyl)carbamoyloxy]-1-azoniabicyclo[2.2.2]octane; chloride The yield was 23 mg (9%) as a brown solid. $^1$H-NMR (CDCl$_3$): 7.30-7.02 (m, 10H), 6.97 (t, 2H), 5.14 (m, 1H), 4.77 (s, 2H), 4.19 (m, 1H), 4.09-3.50 (m, 5H), 3.69 (t, 2H), 3.20 (m, 1H), 2.90 (m, 1H), 2.50-1.80 (m, 6H), 2.17 (s, 3H), 1.58 (m, 1H).

Example 36

(R)-1-{3-[Benzyloxycarbonyl-(2-fluorophenyl)amino]propyl}-3-[(4-fluorobenzyl)-(2-fluorophenyl)carbamoyloxy]-1-azoniabicyclo[2.2.2]octane; chloride The yield was 410 mg (65%) as a white solid. $^1$H-NMR (CDCl$_3$): 7.38-7.02 (m, 15H), 6.96 (t, 2H), 5.09 (s, 2H), 5.08 (m, 1H), 4.76 (dd, 2H), 4.20-3.30 (m, 6H), 3.72 (t, 2H), 3.05 (m, 1H), 2.77 (m, 1H), 2.27 (m, 1H), 2.10-1.80 (m, 5H) 1.56 (m, 1H).

Example 37

(R)-3-[(4-Fluorobenzyl)-(2-fluorophenyl)carbamoyloxy]-1-(2-phenylcarbamoylethyl)-1-azoniabicyclo[2.2.2]octane; chloride The yield was 95 mg (66%) as a yellow solid. $^1$H-NMR (CDCl$_3$): 10.95 (s, 1H), 7.79 (d, 2H), 7.31-7.00 (m, 9H), 6.95 (t, 2H), 5.11 (m, 1H), 4.75 (s, 2H), 4.09 (m, 1H), 3.95-3.10 (m, 6H), 2.87 (m, 1H), 2.29 (m, 1H), 2.10-1.70 (m, 5H) 1.58 (m, 1H).

Example 38

(R)-1-(3-Benzoyloxypropyl)-3-[(4-fluorobenzyl)-(2-fluorophenyl)carbamoyloxy]-1-azoniabicyclo[2.2.2]octane; bromide The yield was 22 mg (13%) as a yellow solid. $^1$H-NMR (CDCl$_3$): 8.02 (m, 2H), 7.56 (m, 1H), 7.45 (m, 2H), 7.30-6.92 (m, 8H), 5.15 (m, 1H), 4.75 (s, 2H), 4.43 (m, 2H), 4.15 (m, 1H), 4.05-3.77 (m, 5H), 3.18 (m, 1H), 2.87 (m, 1H), 2.42-1.80 (m, 6H), 1.56 (m, 1H).

Example 39

(R)-1-[2-(4-acetylaminophenylsulfanyl)ethyl]-3-[(4-fluorobenzyl)-(3-fluorophenyl)carbamoyloxy]-1-azoniabicyclo[2.2.2]octane; bromide The yield was 99 mg (33%) as a yellow solid. $^1$H-NMR (CDCl$_3$): 9.66 (s, 1H), 7.62 (d, 2H), 7.26-7.14 (m, 6H), 7.00-6.90 (m, 6H), 5.05 (m, 1H), 4.80 (m, 2H), 4.10 (m, 1H), 3.90-3.40 (m, 6H), 3.10 (m, 3H), 2.30 (m, 1H), 2.17 (s, 3H), 2.10-1.50 (m, 4H).

Example 40

(3R,2'RS)-3-[(3,4-Difluorobenzyl)phenylcarbamoyloxy]-1-[3-(4-fluorophenoxy)-2-hydroxypropyl]-1-azoniabicyclo[2.2.2]octane; hydroxide The yield was 18 mg (8%), as a yellow oil. $^1$H-NMR (CDCl$_3$): 7.45-7.80 (m, 12H), 6.38 (br, 1H), 5.12 (m, 1H), 4.90-4.58 (m, 3H), 4.35-4.15 (m, 1H), 4.10-3.44 (m, 8H), 3.10 (br, 1H), 2.35 (m, 1H), 2.10-1.60 (m, 4H).

Example 41

(R)-1-[2-(3-Chloro-5-fluorophenyl)ethyl]-3-[(3,4-difluorobenzyl)-(2-fluorophenyl)carbamoyloxy]-1-azoniabicyclo[2.2.2]octane; chloride The yield was 101 mg, as a white solid. $^1$H-NMR (CDCl$_3$): 7.67 (m, 1H), 7.38-6.85 (m, 9H), 5.17 (m, 1H), 4.76 (s, 2H), 4.33-3.70 (m, 7H), 3.57 (m, 1H), 3.33 (m, 1H), 3.17 (m, 2H), 2.99 (m, 1H), 2.35 (m, 1H), 2.10-1.80 (m, 3H), 1.60 (m, 1H).

Example 42

(R)-1-(2-Cyclohexylsulfanylethyl)-3-[(3,4-difluorobenzyl)-(2-fluorophenyl)carbamoyloxy]-1-azoniabicyclo[2.2.2]octane; chloride The yield was 58 mg (28%) as a yellow oil. $^1$H-NMR (CDCl$_3$): 7.30 ((m, 1H), 7.20-7.00 (m, 5H), 6.95 (m, 1H), 5.13 (m, 1H), 4.75 (s, 2H), 4.25-4.25 (m, 2H), 4.00-3.80 (m, 1H), 3.73 (m, 2H), 3.50 (m, 1H), 3.27 (m, 1H), 2.88 (m, 4H), 2.35 (m, 1H), 2.10-1.80 (m, 4H) 1.80-1.50 (m, 4H), 1.45-1.10 (m, 6H).

Example 43

(R)-1-(2-Benzenesulfonylethyl)-3-[(3,4-difluorobenzyl)-(2-fluorophenyl)carbamoyloxy]-1-azoniabicyclo[2.2.2]octane; chloride The yield was 43 mg (20%) as a yellow oil. $^1$H-NMR (CDCl$_3$): 7.35-6.90 (m, 12H), 5.08 (m, 1H), 4.74 (s, 2H), 4.15-3.85 (m, 3H), 3.75-3.45 (m, 4H), 3.20-3.05 (m, 1H), 2.95-2.80 (m, 1H), 2.71 (t, 2H), 2.35 (m, 1H), 2.10-1.70 (m, 4H).

Example 44

(R)-3-[(3,4-Difluorobenzyl)-m-tolylcarbamoyloxy]-1-(2-phenylsulfanylethyl)-1-azoniabicyclo[2.2.2]octane; chloride The yield was 170 mg (63%) as white solid. $^1$H-NMR (CDCl$_3$): 7.58 (s, 2H), 7.36-6.94 (m, 10H), 5.57 (m, 2H), 5.06 (m, 1H), 4.74 (s, 2H), 4.13 (m, 1H), 4.00-3.40 (m, 6H), 3.10 (br, 1H), 2.32 (m, 1H), 2.32 (s, 3H), 2.20-1.50 (m, 4H).

Example 45

(R)-3-[(3,4-Difluorobenzyl)-m-tolylcarbamoyloxy]-1-[3-(4-fluorophenylsulfanyl)propyl]-1-azoniabicyclo[2.2.2]octane; chloride The yield was 96 mg (43%) as a green solid. $^1$H-NMR (CDCl$_3$): 7.40 (dd, 2H), 7.25-6.80 (m, 9H), 5.09 (m, 1H), 4.72 (m, 2H), 4.11 (m, 1H), 3.90-3.60 (m, 5H), 3.27 (m, 1H), 2.96 (t, 2H), 2.64 (m, 1H), 2.31 (m, 1H), 2.31 (s, 3H), 2.10-1.70 (m, 5H), 1.55 (m, 1H).

Example 46

(R)-3-[(3,4-Difluorobenzyl)-(3-fluorophenyl)carbamoyloxy]-1-(2-phenoxyethyl)-1-azoniabicyclo[2.2.2]octane; bromide The yield was 145 mg (56%) as a white solid. $^1$H-NMR (CDCl$_3$): 7.37-7.16 (m, 3H), 7.15-6.96 (m, 6H), 6.94-6.80 (m, 3H), 5.11 (m, 1H), 4.81 (m, 2H), 4.50-4.12 (m, 6H), 4.10-3.70 (m, 3H), 3.45 (br, 1H), 2.32 (m, 1H), 2.02 (m, 2H), 1.90-1.60 (m, 2H).

Example 47

(R)-3-[(3,4-Difluorobenzyl)-(3-fluorophenyl)carbamoyloxy]-1-(3-phenylpropyl)-1-azoniabicyclo[2.2.2]octane; bromide The yield was 151 mg (67%) as a white. $^1$H-NMR (CDCl$_3$): 7.37-6.82 (m, 12H), 5.09 (m, 1H), 4.78 (m, 2H), 4.07 (m, 1H), 3.68 (m, 5H), 3.25 (br, 1H 3.00 (br, 1H), 2.70 (m, 2H), 2.32 (m, 1H), 2.20-1.60 (m, 6H).

Example 48

(R)-1-Cyclopropylmethyl-3-[(2-fluorophenyl)-(3,4,5-trifluorobenzyl)carbamoyloxy]-1-azoniabicyclo[2.2.2]octane; bromide The yield was 107 mg (54%) as a white solid. $^1$H-NMR (CDCl$_3$): 7.40-7.05 (m, 4H), 6.90 (m, 1H), 6.89 (dd, 1H), 5.13 (m, 1H), 4.74 (s, 2H), 4.20-3.90 (m, 3H), 3.85-3.60 (m, 2H), 3.55 (m, 2H), 3.38 (m, 1H), 3.09 (m, 1H), 2.35 (m, 1H), 2.20-1.85 (m, 3H) 1.54 (m, 1H), 0.93 (m, 1H), 0.80 (m, 2H), 0.57 (m, 2H).

Example 49

(R)-1-Benzyl-3-[(2-fluorophenyl)-(3,4,5-trifluorobenzyl)carbamoyloxy]-1-azoniabicyclo[2.2.2]octane; bromide The yield was 119 mg (56%) as a white solid. $^1$H-NMR (CDCl$_3$): 7.55 (m, 2H), 7.44 (s, 3H), 7.32-7.05 (m, 4H), 7.00-6.89 (m, 2H), 5.08 (m, 2H), 4.91 (m, 1H), 4.69 (s, 2H), 4.07 (m, 4H), 3.77 (m, 2H), 3.32 (br, 1H), 2.95 (br, 1H), 2.31 (m, 1H), 2.20-1.45 (m, 4H).

Example 50

(R)-3-[(2-Fluorophenyl)-(3,4,5-trifluorobenzyl)carbamoyloxy]-1-(2-phenylsulfanylethyl)-1-azoniabicyclo[2.2.2]octane; chloride The yield was 36 mg (17%) as a yellow solid. $^1$H-NMR (CDCl$_3$): 7.46-7.22 (m, 6H), 7.20-7.02 (m, 3H), 6.96-6.83 (m, 2H), 5.12 (m, 1H), 4.73 (s, 2H), 4.25-3.95 (m, 3H), 3.80-3.50 (m, 3H), 3.45-3.20 (m, 3H), 2.90 (br, 1H), 2.33 (m, 1H), 2.10-1.80 (m, 3H), 1.59 (m, 1H).

Example 51

(R)-3-[(3-Fluorophenyl)-(3,4,5-trifluorobenzyl)carbamoyloxy]-1-(3-phenoxypropyl)-1-azoniabicyclo[2.2.2]octane; bromide The yield was 126 mg (55%) as a white solid. $^1$H-NMR (CDCl$_3$): 7.40-7.21 (m, 3H), 7.10-6.80 (m, 9H), 5.13 (m, 1H), 4.82 (m, 2H), 4.16 (m, 1H), 4.06 (t, 2H), 4.00-3.60 (m, 6H), 3.30 (br, 1H), 2.38 (m, 1H), 2.25 (m, 2H), 2.15-1.60 (m, 4H).

Example 52

(R)-1-[3-(3,4-Difluorophenoxy)propyl]-3-[(3-fluorophenyl)-(3,4,5-trifluorobenzyl)carbamoyloxy]-1-azoniabicyclo[2.2.2]octane; chloride $^1$H-NMR (CDCl$_3$): 7.33 (m, 1H), 7.12-6.85 (m, 6H), 6.69 (ddd, 1H), 6.57 (m, 1H), 5.16 (m, 1H), 4.83 (m, 2H), 4.18 (m, 1H), 4.04 (t, 2H), 4.00-3.60 (m, 6H), 3.30 (br, 1H), 2.38 (m, 1H), 2.34 (m, 2H), 2.15-1.60 (m, 4H).

Example 53

(R)-1-(2-Oxo-2-phenylethyl)-3-(thiophen-2-ylmethyl-m-tolylcarbamoyloxy)-1-azoniabicyclo[2.2.2]octane; bromide The yield was 23 mg (15%) as a white solid. $^1$H-NMR (CDCl$_3$): 8.09 (d, 2H), 7.56 (t, 1H), 7.42 (t, 2H), 7.23 (dd, 1H), 7.21 (s, 1H), 7.13-6.96 (m, 3H), 6.93-6.83 (m, 2H), 5.79 (s, 2H), 5.15 (m, 1H), 4.95 (m, 2H), 4.60-3.80 (m, 4H), 3.61 (m, 1H), 3.29 (m, 1H), 2.33 (m, 1H), 2.32 (s, 3H), 2.20-1.50 (m, 4H).

Example 54

(R)-1-(3-Phenylpropyl)-3-(thiophen-2-ylmethyl-m-tolylcarbamoyloxy)-1-azoniabicyclo[2.2.2]octane; bromide The yield was 36 mg (23%) as a white solid. $^1$H-NMR (CDCl$_3$): 7.34-7.18 (m, 5H), 7.08 (d, 1H), 7.01 (d, 1H), 6.94-6.82 (m, 5H), 5.11 (m, 1H), 4.92 (s, 2H), 4.45-3.90 (m, 6H), 3.85-3.60 (m, 2H), 3.15 (m, 1H), 3.01 (m, 1H), 2.41 (m, 1H), 2.31 (s, 3H), 2.20-1.61 (m, 4H).

Example 55

(R)-1-Benzyl-3-[(2-fluorophenyl)thiophen-2-ylmethylcarbamoyloxy]-1-azoniabicyclo[2.2.2]octane; bromide The yield was 163 mg (75%) as a yellow solid. $^1$H-NMR (CDCl$_3$): 7.75-7.35 (m, 5H), 7.25-6.82 (m, 7H), 5.12 (m, 1H), 5.20-4.80 (m, 5H), 4.40-3.40 (m, 4H), 3.19 (m, 1H), 3.01 (t, 2H), 2.79 (m, 1H), 2.27 (m, 1H), 2.20-1.50 (m, 4H).

Example 56

(R)-1-Cyclobutylmethyl-3-[(3-fluorophenyl)thiophen-2-ylmethylcarbamoyloxy]-1-azoniabicyclo[2.2.2]octane; bromide The yield was 153 mg (72%) as an oil. $^1$H-NMR (CDCl$_3$): 7.33 (td, 1H), 7.25 (dd, 1H), 7.05-6.88 (m, 5H), 5.15 (m, 1H), 5.00 (m, 2H), 4.15-4.00 (m, 1H), 3.80-3.95 (m, 2H), 3.70-3.50 (m, 1H), 3.60 (dd, 2H), 3.30 (m, 1H), 2.73 (m, 1H), 2.42 (m, 1H), 2.20-0.90 (m, 11H).

Example 57

(R)-3-[(3-Methylthiophen-2-ylmethyl)phenylcarbamoyloxy]-1-(2-phenoxyethyl)-1-azoniabicyclo[2.2.2]octane; bromide The yield was 170 mg (56%) as an oil. $^1$H-NMR (CDCl$_3$): 7.35-7.25 (m, 1H), 7.32 (t, 2H), 7.10-6.80 (m, 6H), 6.58 (m, 1H), 6.51 (m, 1H), 5.13 (m, 1H), 4.87 (m, 2H), 4.55-4.30 (m, 3H), 4.30-4.00 (m, 4H), 3.80 (m, 2H), 3.15 (br, 1H), 2.42 (m, 1H), 2.41 (s, 3H), 2.20-1.50 (m, 4H).

Example 58

(R)-3-[(4-Bromothiophen-2-ylmethyl)phenylcarbamoyloxy]-1-Cyclopropylmethyl-1-azoniabicyclo[2.2.2]octane; bromide The yield was 90 mg (60%) as a white solid. $^1$H-NMR (CDCl$_3$): 7.43-7.28 (m, 3H), 7.28-7.10 (m, 2H), 7.15 (d, 1H), 6.83 (s, 1H), 5.12 (m, 1H), 4.91 (m, 2H), 4.17 (ddd, 1H), 4.05-3.30 (m, 4H), 3.57 (d, 2H), 2.93 (br, 1H), 2.35 (m, 1H), 2.20-1.50 (m, 4H), 0.97 (br, 1H), 0.78 (m, 2H), 0.56 (m, 2H).

Example 59

(R)-3-[(4-Bromothiophen-2-ylmethyl)phenylcarbamoyloxy]-1-phenylsulfanylmethyl-1-azoniabicyclo[2.2.2]octane; chloride The yield was 89 mg (57%) as a white solid. $^1$H-NMR (CDCl$_3$): 7.68 (m, 1H), 7.58 (br, 3H), 7.45-7.30 (m, 6H), 7.13 (m, 2H), 6.81 (s, 1H), 5.54 (m, 2H), 5.07 (m, 1H), 4.90 (m, 2H), 4.12 (m, 1H), 3.90-3.60 (m, 3H), 3.45 (m, 1H), 3.11 (m, 1H), 2.33 (m, 1H), 2.20-1.50 (m, 4H).

Example 60

(R)-1-[2-(2,3-Dihydrobenzofuran-5-yl)ethyl]-3-[(5-methylthiophen-2-ylmethyl)phenylcarbamoyloxy]-1-azoniabicyclo[2.2.2]octane; bromide The yield was 310 mg (63%) as a white solid. $^1$H-NMR (CDCl$_3$): 7.36-7.05 (m, 5H), 7.29 (d, 1H), 7.15 (s, 1H), 6.93 (d, 1H), 6.61 (d, 1H), 6.54 (d, 1H), 5.08 (m, 1H), 4.83 (m, 2H), 4.47 (t, 2H), 4.13 (ddd, 1H), 4.09-3.80 (m, 2H), 3.80-3.50 (m, 3H), 3.20 (br, 1H), 3.09 (t, 2H), 2.89 (t, 2H), 2.85 (br, 1H), 2.39 (s, 3H), 2.29 (m, 1H), 2.21-1.80 (m, 4H), 1.52 (br, 1H).

Example 61

(R)-3-[(5-Chlorothiophen-2-ylmethyl)-(2-fluorophenyl)carbamoyloxy]-1-(2-phenoxyethyl)-1-azoniabicyclo[2.2.2]octane; bromide The yield was 200 mg (98%) as a yellow solid. $^1$H-NMR (CDCl$_3$): 7.40-7.20 (m, 4H), 7.15-6.95 (m, 3H), 6.95-6.80 (m, 2H), 6.69 (br, 1H), 6.61 (br, 1H), 5.13 (m, 1H), 4.80 (s, 2H), 4.60-4.00 (m, 8H), 3.53 (m, 1H), 3.06 (m, 1H), 2.40 (m, 1H), 2.20-1.50 (m, 4H).

Example 62

(R)-3-[(5-Bromothiophen-2-ylmethyl)phenylcarbamoyloxy]-1-Cyclopropylmethyl-1-azoniabicyclo[2.2.2]octane; bromide The yield was 100 mg (60%) as a white solid. $^1$H-NMR (CDCl$_3$): 7.45-7.25 (m, 3H), 7.25-7.09 (m, 2H), 6.87 (d, 1H), 6.64 (br, 1H), 5.12 (m, 1H), 4.89 (m, 2H), 4.40 (m, 1H), 4.17 (m, 1H), 4.05-3.80 (m, 2H), 3.80-3.05 (m, 6H), 2.36 (m, 1H), 2.20-1.50 (m, 4H), 0.95 (m, 1H), 0.81 (m, 2H), 0.58 (m, 2H).

Example 63

(R)-3-[(5-Bromothiophen-2-ylmethyl)phenylcarbamoyloxy]-1-(2-phenylsulfanylethyl)-1-azoniabicyclo[2.2.2]octane; chloride The yield was 50 mg (28%) as a white solid. $^1$H-NMR (CDCl$_3$): 7.47-7.20 (m, 8H), 7.13 (br, 2H), 6.85 (d, 1H), 6.62 (d, 1H), 5.11 (m, 1H), 4.84 (s, 2H), 4.15 (m, 1H), 4.00 (m, 2H), 3.85-3.50 (m, 4H), 3.45-3.20 (m, 2H), 2.95 (br, 1H), 2.33=(m, 1H), 2.20-1.80 (m, 3H), 1.62 (m, 1H).

Example 64

(R)-3-[(5-Bromothiophen-2-ylmethyl)-m-tolylcarbamoyloxy]-1-phenylsulfanylmethyl-1-azoniabicyclo[2.2.2]octane; chloride The yield was 83 mg (79%) as a yellow solid. $^1$H-NMR (CDCl$_3$): 7.58 (m, 2H), 7.46-7.31 (m, 3H), 7.21 (d, 1H), 7.12 (m, 1H), 7.02-6.86 (m, 2H), 6.86 (d, 1H), 6.64 (m, 1H), 5.55 (m, 2H), 5.07 (m, 1H), 4.83 (s, 2H), 4.15-3.60 (m, 4H), 3.40 (br, 1H), 3.05 (br, 1H), 2.34 (s, 3H), 2.33 (m, 1H), 2.20-1.50 (m, 4H).

Example 65

(R)-3-[(5-Bromothiophen-2-ylmethyl)-(4-fluorophenyl)carbamoyloxy]-1-cyclopropylmethyl-1-azoniabicyclo[2.2.2]octane; bromide The yield was 81 mg (62%) as a brownish solid. $^1$H-NMR (CDCl$_3$): 7.32-7.12 (m, 2H), 7.04 (t, 2H), 6.87 (d, 1H), 6.63 (m, 1H), 5.11 (m, 1H), 5.05-4.60 (m, 2H), 4.15 (m, 1H), 4.00-3.70 (m, 3H), 3.65-3.45 (m, 3H), 3.15 (br, 1H), 2.37 (m, 1H), 2.15-1.55 (m, 4H), 0.98 (m, 1H), 0.80 (m, 2H), 0.59 (m, 2H).

Example 66

(R)-3-[(5-Bromothiophen-2-ylmethyl)-(4-fluorophenyl)carbamoyloxy]-1-(2-oxo-2-phenylethyl)-1-azoniabicyclo[2.2.2]octane; bromide The yield was 110 mg (76%) as a yellow solid. $^1$H-NMR (CDCl$_3$): 8.12 (d, 2H), 7.58 (t, 1H), 7.42 (t, 2H), 7.36-7.24 (m, 2H), 7.03 (t, 2H), 6.86 (d, 1H), 6.63 (m, 1H), 5.85 (s, 2H), 5.18 (m, 1H), 5.00 (m, 1H), 4.75-3.90 (m, 6H), 3.66 (m, 1H), 2.35 (m, 1H), 2.15-1.55 (m, 4H).

Example 67

(R)-3-[(5-Bromothiophen-2-ylmethyl)(4-fluorophenyl)carbamoyloxy]-1-(3-phenylpropyl)-1-azoniabicyclo[2.2.2]octane; bromide The yield was 107 mg (73%) as a yellow solid. $^1$H-NMR (CDCl$_3$): 7.33-7.15 (m, 7H), 7.02 (t, 2H), 6.84 (d, 1H), 6.61 (m, 1H), 5.09 (m, 1H), 5.02-4.60 (m, 2H), 4.12 (m, 1H), 3.80-3.55 (m, 5H), 3.45 (br, 1H), 3.10 (br, 1H), 2.70 (t, 2H), 2.50-1.75 (m, 7H), 1.60 (m, 1H).

Example 68

(R)-1-Cyclobutylmethyl-3-[(3-fluorophenyl)thiophen-3-ylmethylcarbamoyloxy]-1-azoniabicyclo[2.2.2]octane; bromide The yield was 89 mg (42%) as white solid. $^1$H-NMR (CDCl$_3$): 7.40-7.30 (m, 3H), 7.16 (s, 1H), 7.03-6.87 (m, 3H), 5.11 (m, 1H), 4.86 (m, 2H), 4.08 (m, 1H), 3.90-3.70 (m, 2H), 3.70-3.50 (m, 1H), 3.59 (d, 2H), 3.35 (m, 1H), 3.02 (m, 1H), 2.72 (m, 1H), 2.36 (m, 1H), 2.20-0.90 (m, 11H).

Example 69

(R)-3-[(3-Fluorophenyl)thiophen-3-ylmethylcarbamoyloxy]-1(2-oxo-2-phenylethyl)-1-azoniabicyclo[2.2.2]octane; bromide The yield was 161 mg (68%) as a white solid. $^1$H-NMR (CDCl$_3$): 8.10 (d, 2H), 7.56 (t, 1H), 7.43 (t, 2H), 7.32-7.18 (m, 3H), 7.14 (m, 1H), 7.05-6.85 (m, 3H), 5.86 (s, 2H), 5.16 (m, 1H), 4.77 (m, 2H), 4.60-3.90 (m, 5H), 3.70 (m, 1H), 2.34 (m, 1H), 2.20-1.50 (m, 4H).

Example 70

(R)-3-Cyclohexylmethylphenylcarbamoyloxy-1-(2-oxo-2-phenylethyl)-1-azoniabicyclo[2.2.2]octane; bromide The yield was 120 mg (75%) as an oil. $^1$H-NMR (CDCl$_3$): 8.10 (d, 2H), 7.58 (t, 1H), 7.43 (t, 2H), 7.40-7.20 (m, 5H), 5.75 (s, 2H), 5.09 (m, 1H), 4.51-3.90 (m, 5H), 3.55 (d, 2H), 2.95 (br, 1H), 2.35 (m, 1H), 2.15-0.90 (m, 15H).

Example 71

(R)-3-Cyclohexylmethylphenylcarbamoyloxy)-1-(3-phenoxypropyl)-1-azoniabicyclo[2.2.2]octane; bromide The yield was 40 mg (35%) as an oil. $^1$H-NMR (CDCl$_3$): 7.34 (t, 2H), 7.30-7.15 (m, 4H), 7.05 (t, 2H), 6.88 (d, 2H), 5.07 (m, 1H), 4.55-3.90 (m, 6H), 3.87-3.60 (m, 3H), 3.48 (d, 2H), 2.95 (br, 1H), 2.35 (m, 1H), 2.15-0.90 (m, 15H).

The following compounds were also prepared, and they have been identified by $^1$H-NMR:

(R)-3-(Benzylphenylcarbamoyloxy)-1-Cyclopropylmethyl-1-azoniabicyclo[2.2.2]octane, bromide
(R)-3-(Benzylphenylcarbamoyloxy)-1-Cyanomethyl-1-azoniabicyclo[2.2.2]octane; bromide
(R)-1-Benzyl-3-(benzylphenylcarbamoyloxy)-1-azoniabicyclo[2.2.2]octane; bromide
(R)-3-(Benzylphenylcarbamoyloxy)-1-[2-(2,3-dihydrobenzofuran-5-yl)ethyl]-1-azoniabicyclo[2.2.2]octane; bromide
(R)-3-(Benzylphenylcarbamoyloxy)-1-(4-methoxybenzyl)-1-azoniabicyclo[2.2.2]octane; chloride
(R)-3-(Benzylphenylcarbamoyloxy)-1-(2-oxo-2-phenylethyl)-1-azoniabicyclo[2.2.2]octane; bromide
(R)-3-(Benzylphenylcarbamoyloxy)-1-(2-phenoxyethyl)-1-azoniabicyclo[2.2.2]octane; bromide
(R)-3-(Benzylphenylcarbamoyloxy)-1-[2-(4-fluorophenoxy)ethyl]-1-azoniabicyclo[2.2.2]octane; chloride
(R)-3-(Benzylphenylcarbamoyloxy)-1-(3-phenylpropyl)-1-azoniabicyclo[2.2.2]octane; bromide
(R)-3-(Benzylphenylcarbamoyloxy)-1-(3-phenoxypropyl)-1-azoniabicyclo[2.2.2]octane; chloride
(R)-3-(Benzylphenylcarbamoyloxy)-1-[3-(4-fluorophenoxy)-2-hydroxypropyl]-1-azoniabicyclo[2.2.2]octane; hydroxide
(R)-1-Cyclobutylmethyl-3-[(4-fluorobenzyl)phenylcarbamoyloxy]-1-azoniabicyclo[2.2.2]octane; bromide
(R)-1-Benzyl-3-[(4-fluorobenzyl)phenylcarbamoyloxy]-1-azoniabicyclo[2.2.2]octane; bromide
(R)-3-[(4-Fluorobenzyl)phenylcarbamoyloxy]-1-phenylsulfanylmethyl-1-azoniabicyclo[2.2.2]octane; chloride
(R)-3-[(4-Fluorobenzyl)phenylcarbamoyloxy]-1-phenethyl-1-azoniabicyclo[2.2.2]octane; bromide
(R)-3-[(4-Fluorobenzyl)phenylcarbamoyloxy]-1-(2-o-tolylethyl)-1-azoniabicyclo[2.2.2]octane; bromide
(R)-3-[(4-Fluorobenzyl)phenylcarbamoyloxy]-1-[2-(2-methoxyphenyl)ethyl]-1-azoniabicyclo[2.2.2]octane; bromide
(R)-3-[(4-Fluorobenzyl)phenylcarbamoyloxy]-1-[2-(3-methoxyphenyl)ethyl]-1-azoniabicyclo[2.2.2]octane; bromide
(R)-3-[(4-Fluorobenzyl)phenylcarbamoyloxy]-1-[2-(3-fluorophenyl)ethyl]-1-azoniabicyclo[2.2.2]octane; bromide
(R)-3-[(4-Fluorobenzyl)phenylcarbamoyloxy]-1-[2-(4-p-tolylethyl)-1-azoniabicyclo[2.2.2]octane; bromide
(R)-3-[(4-Fluorobenzyl)phenylcarbamoyloxy]-1-[2-(4-fluorophenyl)ethyl]-1-azoniabicyclo[2.2.2]octane; bromide
(R)-1-[2-(2,5-Dimethoxyphenyl)ethyl]-3-[(4-fluorobenzyl)phenylcarbamoyloxy]-1-azoniabicyclo[2.2.2]octane; bromide
(R)-1-[2-(3,4-Dimethoxyphenyl)ethyl]-3-[(4-fluorobenzyl)phenylcarbamoyloxy]-1-azoniabicyclo[2.2.2]octane; bromide.
(R)-3-[(4-Fluorobenzyl)phenylcarbamoyloxy]-1-(2-oxo-2-phenylethyl)-1-azoniabicyclo[2.2.2]octane; bromide
(R)-3-[(4-Fluorobenzyl)phenylcarbamoyloxy]-1-[2-(4-fluorophenoxy)ethyl]-1-azoniabicyclo[2.2.2]octane; bromide
(R)-3-[(4-Fluorobenzyl)phenylcarbamoyloxy]-1-[2-(2-fluorophenylsulfanyl)ethyl]-1-azoniabicyclo[2.2.2]octane; bromide
(R)-3-[(4-Fluorobenzyl)-m-tolylcarbamoyloxy]-1-phenethyl-1-azoniabicyclo[2.2.2]octane; bromide
(R)-1-[2-(2,3-Dihydrobenzofuran-5-yl)ethyl]-3-[(4-fluorobenzyl)-m-tolylcarbamoyloxy]-1-azoniabicyclo[2.2.2]octane; bromide
(R)-3-[(4-Fluorobenzyl)-m-tolylcarbamoyloxy]-1-(2-oxo-2-phenylethyl)-1-azoniabicyclo[2.2.2]octane; bromide
(R)-3-[(4-Fluorobenzyl)-m-tolylcarbamoyloxy]-1-(2-phenoxyethyl)-1-azoniabicyclo[2.2.2]octane; bromide
(R)-3-[(4-Fluorobenzyl)-m-tolylcarbamoyloxy]-1-(3-phenylpropyl)-1-azoniabicyclo[2.2.2]octane; bromide
(R)-3-[(4-Fluorobenzyl)-m-tolylcarbamoyloxy]-1-(3-phenoxypropyl)-1-azoniabicyclo[2.2.2]octane; bromide
(R)-3-[(4-Fluorobenzyl)-(2-fluorophenyl)carbamoyloxy]-1-phenylsulfanylmethyl-1-azoniabicyclo[2.2.2]octane; chloride
(R)-3-[(4-Fluorobenzyl)-(2-fluorophenyl)carbamoyloxy]-1-(2-o-tolylethyl)-1-azoniabicyclo[2.2.2]octane; bromide
(R)-3-[(4-Fluorobenzyl)-(2-fluorophenyl)carbamoyloxy]-1-[2-(2-methoxyphenyl)ethyl]-1-azoniabicyclo[2.2.2]octane; bromide
(R)-3-[(4-Fluorobenzyl)-(2-fluorophenyl)carbamoyloxy]-1-(2-m-tolylethyl)-1-azoniabicyclo[2.2.2]octane; bromide
(R)-3-[(4-Fluorobenzyl)-(2-fluorophenyl)carbamoyloxy]-1-[2-(3-methoxyphenyl)ethyl]-1-azoniabicyclo[2.2.2]octane; bromide
(R)-3-[(4-Fluorobenzyl)-(2-fluorophenyl)carbamoyloxy]-1-[2-(3-fluorophenyl)ethyl]-1-azoniabicyclo[2.2.2]octane; bromide
(R)-3-[(4-Fluorobenzyl)-(2-fluorophenyl)carbamoyloxy]-1-(2-p-tolylethyl)-1-azoniabicyclo[2.2.2]octane; bromide
(R)-3-[(4-Fluorobenzyl)-(2-fluorophenyl)carbamoyloxy]-1-[2-(4-methoxyphenyl)ethyl]-1-azoniabicyclo[2.2.2]octane; bromide
(R)-1-[2-(4-Ethoxyphenyl)ethyl]-3-[(4-fluorobenzyl)-(2-fluorophenyl)carbamoyloxy]-1-azoniabicyclo[2.2.2]octane; bromide
(R)-3-[(4-Fluorobenzyl)-(2-fluorophenyl)carbamoyloxy]-1-[2-(4-fluorophenyl)ethyl]-1-azoniabicyclo[2.2.2]octane; bromide
(R)-1-[2-(2,5-Dimethoxyphenyl)ethyl]-3-[(4-fluorobenzyl)-(2-fluorophenyl)carbamoyloxy]-1-azoniabicyclo[2.2.2]octane; bromide
(R)-3-[(4-Fluorobenzyl)-(2-fluorophenyl)carbamoyloxy]-1-phenylcarbamoylmethyl-1-azoniabicyclo[2.2.2]octane; bromide
(R)-3-[(4-Fluorobenzyl)-(2-fluorophenyl)carbamoyloxy]-1-(o-tolylcarbamoylmethyl)-1-azoniabicyclo[2.2.2]octane; bromide
(R)-3-[(4-Fluorobenzyl)-(2-fluorophenyl)carbamoyloxy]-1-[2-(2-fluorophenoxy)ethyl]-1-azoniabicyclo[2.2.2]octane; bromide (R)-3-[(4-Fluorobenzyl)-(2-fluorophenyl)carbamoyloxy]-1-[2-(3-methoxyphenoxy)ethyl]-1-azoniabicyclo[2.2.2]octane; bromide (R)-3-[(4-Fluorobenzyl)-(2-fluorophenyl)carbamoyloxy]-1-[2-(4-fluorophenoxy)ethyl]-1-azoniabicyclo[2.2.2]octane; bromide (R)-3-[(4-Fluorobenzyl)-(2-fluorophenyl)carbamoyloxy]-1-(2-phenylsulfanylethyl)-1-azoniabicyclo[2.2.2]octane; chloride (R)-3-[(4-Fluorobenzyl)-(2-fluorophenyl)carbamoyloxy]-1-[2-(2-metoxyphenylsulfanyl)ethyl]-1-azoniabicyclo[2.2.2]octane; chloride (R)-3-[(4-Fluorobenzyl)-(2-fluorophenyl)carbamoyloxy]-1-[2-(2-fluorophenylsulfanyl)ethyl]-1-azoniabicyclo[2.2.2]octane; chloride (R)-1-[2-(2-Chlorophenylsulfanyl)ethyl]-3-[(4-fluorobenzyl)-(2-fluorophenyl)carbamoyloxy]-1-azoniabicyclo[2.2.2]octane; chloride (R)-1-[2-(3-Chlorophenylsulfanyl)ethyl]-3-[(4-fluorobenzyl)-(2-fluorophenyl)carbamoyloxy]-1-azoniabicyclo[2.2.2]octane; chloride (R)-3-[(4-Fluorobenzyl)-(2-fluorophenyl)carbamoyloxy]-1-[2-(4-fluorophenylsulfanyl)ethyl]-1-azoniabicyclo[2.2.2]octane; chloride (R)-1-[2-(4-Bromophenylsulfanyl)ethyl]-3-[(4-fluorobenzyl)-(2-fluorophenyl)carbamoyloxy]-1-azoniabicyclo[2.2.2]octane; chloride (R)-1-[2-(2,4-Difluorophenylsulfanyl)ethyl]-3-[(4-fluorobenzyl)-(2-fluorophenyl)carbamoyloxy]-1-azoniabicyclo[2.2.2]octane; bromide (R)-1-[2-(2,5-Dichlorophenylsulfanyl)ethyl]-3-[(4-fluorobenzyl)-(2-fluorophenyl)carbamoyloxy]-1-azoniabicyclo[2.2.2]octane; bromide (3R,SS) and (3,SR)-1-(2-Benzenesulfinylethyl)-3-[(4-fluorobenzyl)-(2-fluorophenyl)carbamoyloxy]-1-azoniabicyclo[2.2.2]octane; chloride (R)-3-[(4-Fluorobenzyl)-(2-fluorophenyl)carbamoyloxy]-1-(3-phenoxypropyl)-1-azoniabicyclo[2.2.2]octane; bromide (R)-3-[(4-Fluorobenzyl)-(2-fluorophenyl)carbamoyloxy]-1-[3-(2-fluorophenoxy)propyl]-1-azoniabicyclo[2.2.2]octane; chloride (R)-3-[(4-Fluorobenzyl)-(2-fluorophenyl)carbamoyloxy]-1-(3-m-tolyloxypropyl)-1-azoniabicyclo[2.2.2]octane; chloride (R)-3-[(4-Fluorobenzyl)-(2-fluorophenyl)carbamoyloxy]-1-[3-(3-methoxyphenoxy)propyl]-1-azoniabicyclo[2.2.2]octane; chloride (R)-1-[3-(2,4-Difluorophenoxy)propyl]-3-[(4-fluorobenzyl)-(2-fluorophenyl)carbamoyloxy]-1-azoniabicyclo[2.2.2]octane; chloride (R)-3-[(4-Fluorobenzyl)-(2-fluorophenyl)carbamoyloxy]-1-[3-(pyridin-3-yloxy)propyl]-1-azoniabicyclo[2.2.2]octane; chloride (R)-3-[(4-Fluorobenzyl)-(2-fluorophenyl)carbamoyloxy]-1-[3-(pyrimidin-2-yloxy)propyl]-1-azoniabicyclo[2.2.2]octane; chloride (R)-3-[(4-Fluorobenzyl)-(2-fluorophenyl)carbamoyloxy]-1-(3-phenylsulfanylpropyl)-1-azoniabicyclo[2.2.2]octane.

(R)-3-[(4-Fluorobenzyl)-(2-fluorophenyl)carbamoyloxy]-1-[3-(2-fluorophenylsulfanyl)propyl]-1-azoniabicyclo[2.2.2]octane; chloride (R)-1-[3-(2-Chlorophenylsulfanyl)propyl]-3-[(4-fluorobenzyl)-(2-fluorophenyl)carbamoyloxy]-1-azoniabicyclo[2.2.2]octane; chloride (R)-1-[3-(3-Chlorophenylsulfanyl)propyl]-3-[(4-fluorobenzyl)-(2-fluorophenyl)carbamoyloxy]-1-azoniabicyclo[2.2.2]octane; chloride (R)-3-[(4-Fluorobenzyl)-(2-fluorophenyl)carbamoyloxy]-1-[3-(pyridin-4-ylsulfanyl)propyl]-1-azoniabicyclo[2.2.2]octane (R)-3-[(4-Fluorobenzyl)-(2-fluorophenyl)carbamoyloxy]-1-[3-(pyrimidin-2-ylsulfanyl)propyl]-1-azoniabicyclo[2.2.2]octane (R)-1-(3-Benzenesulfonylpropyl)-3-[(4-fluorobenzyl)-(2-fluorophenyl)carbamoyloxy]-1-azoniabicyclo[2.2.2]octane; chloride (R)-1-[3-(3-Chlorobenzenesulfonyl)propyl]-3-[(4-fluorobenzyl)-(2-fluorophenyl)carbamoyloxy]-1-azoniabicyclo[2.2.2]octane; chloride (R)-1-{3-[Acetyl-(2-fluorophenyl)amino]propyl}-3-[(4-fluorobenzyl)-(2-fluorophenyl)carbamoyloxy]-1-azoniabicyclo[2.2.2]octane; chloride (R)-1-{3-[Acetyl-(3-methoxyphenyl)amino]propyl}-3-[(4-fluorobenzyl)-(2-fluorophenyl)carbamoyloxy]-1-azoniabicyclo[2.2.2]octane; chloride (R)-1-Benzyl-3-[(4-fluorobenzyl)-(3-fluorophenyl)carbamoyloxy]-1-azoniabicyclo[2.2.2]octane; bromide (R)-3-[(4-Fluorobenzyl)-(3-fluorophenyl)carbamoyloxy]-1-phenylsulfanylmethyl-1-azoniabicyclo[2.2.2]octane; chloride (R)-1-[2-(2-Chlorophenyl)ethyl]-3-[(4-fluorobenzyl)-(3-fluorophenyl)carbamoyloxy]-1-azoniabicyclo[2.2.2]octane; bromide (R)-3-[(4-Fluorobenzyl)-(3-fluorophenyl)carbamoyloxy]-1-[2-(3-fluorophenyl)ethyl]-1-azoniabicyclo[2.2.2]octane; bromide (R)-3-[(4-Fluorobenzyl)-(3-fluorophenyl)carbamoyloxy]-1-[2-(4-methoxyphenyl)ethyl]-1-azoniabicyclo[2.2.2]octane; chloride (R)-3-[(4-Fluorobenzyl)-(3-fluorophenyl)carbamoyloxy]-1-[2-(4-methoxyphenyl)ethyl]-1-azoniabicyclo[2.2.2]octane; bromide (R)-3-[(4-Fluorobenzyl)-(3-fluorophenyl)carbamoyloxy]-1-[2-(4-fluorophenyl)ethyl]-1-azoniabicyclo[2.2.2]octane; bromide (R)-1-[2-(2-Chloro-6-fluorophenyl)ethyl]-3-[(4-fluorobenzyl)-(3-fluorophenyl)carbamoyloxy]-1-azoniabicyclo[2.2.2]octane; bromide (R)-3-[(4-Fluorobenzyl)-(3-fluorophenyl)carbamoyloxy]-1-(2-phenoxyethyl)-1-azoniabicyclo[2.2.2]octane; bromide (R)-3-[(4-Fluorobenzyl)-(3-fluorophenyl)carbamoyloxy]-1-(3-phenylpropyl)-1-azoniabicyclo[2.2.2]octane; bromide (R)-1-[3-(3,4-Difluorophenoxy)propyl]-3-[(4-fluorobenzyl)-(3-fluorophenyl)carbamoyloxy]-1-azoniabicyclo[2.2.2]octane; chloride (R)-1-[3-(3-Chlorophenylsulfanyl)propyl]-3-[(4-fluorobenzyl)-(3-fluorophenyl)carbamoyloxy]-1-azoniabicyclo[2.2.2]octane; chloride (R)-3-[(4-Fluorobenzyl)-(3-fluorophenyl)carbamoyloxy]-1-[3-(4-fluorophenylsulfanyl)propyl]-1-azoniabicyclo[2.2.2]octane; chloride (R)-3-[(3,4-Difluorobenzyl)-(2-fluorophenyl)carbamoyloxy]-1-phenethyl-1-azoniabicyclo[2.2.2]octane; bromide (R)-3-[(3,4-Difluorobenzyl)-(2-fluorophenyl)carbamoyloxy]-1-[2-(4-methoxyphenyl)ethyl]-1-azoniabicyclo[2.2.2]octane; chloride (R)-3-[(3,4-Difluorobenzyl)-(2-fluorophenyl)carbamoyloxy]-1-(2-oxo-2-phenylethyl)-1-azoniabicyclo[2.2.2]octane; bromide (R)-3-[(3,4-Difluorobenzyl)-(2-fluorophenyl)carbamoyloxy]-1-(2-phenoxyethyl)-1-azoniabicyclo[2.2.2]octane; bromide (R)-3-[(3,4-Difluorobenzyl)-(2-fluorophenyl)carbamoyloxy]-1-[2-(4-fluorophenoxy)ethyl]-1-azoniabicyclo[2.2.2]octane; bromide (R)-3-[(3,4-Difluorobenzyl)-(2-fluorophenyl)carbamoyloxy]-1-(2-phenylsulfanylethyl)-1-azoniabicyclo[2.2.2]octane; chloride (3R,2'RS)-3-[(3,4-Difluorobenzyl)-(2-fluorophenyl)carbamoyloxy]-1-[3-(4-fluorophenoxy)-2-hydroxypropyl]-1-azoniabicyclo[2.2.2]octane; hydroxide (R)-3-[(3,4-Difluorobenzyl)-(2-fluorophenyl)carbamoyloxy]-1-(3-phenylpropyl)-1-azoniabicyclo[2.2.2]octane; bromide (R)-3-[(3,4-Difluorobenzyl)-(2-fluorophenyl)carbamoyloxy]-1-[3-(2,4-difluorophenoxy)propyl]-1-azoniabicyclo[2.2.2]octane; chloride (R)-3-[(3,4-Difluorobenzyl)-m-tolylcarbamoyloxy]-1-phenethyl-1-azoniabicyclo[2.2.2]octane; bromide (R)-3-[(3,4-Difluorobenzyl)-m-tolylcarbamoyloxy]-1-[2-(2-fluorophenyl)ethyl]-1-azoniabicyclo[2.2.2]octane; bromide (R)-3-[(3,4-Difluorobenzyl)-m-tolylcarbamoyloxy]-1-[2-(4-methoxyphenyl)ethyl]-1-azoniabicyclo[2.2.2]octane; chloride (R)-3-[(3,4-Difluorobenzyl)-m-tolylcarbamoyloxy]-1-(2-oxo-2-phenylethyl)-1-azoniabicyclo[2.2.2]octane; bromide (R)-3-[(3,4-Difluorobenzyl)-m-tolylcarbamoyloxy]-1-(2-phenoxyethyl)-1-azoniabicyclo[2.2.2]octane; bromide (R)-3-[(3,4-Difluorobenzyl)-m-tolylcarbamoyloxy]-1-[2-(4-fluorophenoxy)ethyl]-1-azoniabicyclo[2.2.2]octane; bromide (R)-3-[(3,4-Difluorobenzyl)-m-tolylcarbamoyloxy]-1-(2-phenylsulfanylethyl)-1-azoniabicyclo[2.2.2]octane; chloride (R)-3-[(3,4-Difluorobenzyl)-m-tolylcarbamoyloxy]-1-(3-phenylpropyl)-1-azoniabicyclo[2.2.2]octane; bromide (R)-3-[(3,4-Difluorobenzyl)-m-tolylcarbamoyloxy]-1-(3-phenoxypropyl)-1-azoniabicyclo[2.2.2]octane; chloride (R)-3-[(3,4-Difluorobenzyl)-m-tolylcarbamoyloxy]-1-(3-phenylsulfanylpropyl)-1-azoniabicyclo[2.2.2]octane; chloride (R)-3-[(3,4-Difluorobenzyl)-m-tolylcarbamoyloxy]-1-[3-(2-fluorophenylsulfanyl)propyl]-1-azoniabicyclo[2.2.2]octane; chloride (R)-1-[3-(3-Chlorophenylsulfanyl)propyl]-3-[(3,4-difluorobenzyl)-m-tolylcarbamoyloxy]-1-azoniabicyclo[2.2.2]octane; chloride (R)-1-Cyclopropylmethyl-3-[(3,4-difluorobenzyl)-(3-fluorophenyl)carbamoyloxy]-1-azoniabicyclo[2.2.2]octane; bromide (R)-3-[(3,4-Difluorobenzyl)-(3-fluorophenyl)carbamoyloxy]-1-phenethyl-1-azoniabicyclo[2.2.2]octane; bromide (R)-3-[(3,4-Difluorobenzyl)-(3-fluorophenyl)carbamoyloxy]-1-[2-(4-methoxyphenyl)ethyl]-1-azoniabicyclo[2.2.2]octane; chloride (R)-3-[(3,4-Difluorobenzyl)-(3-fluorophenyl)carbamoyloxy]-1-[2-(4-methoxyphenyl)ethyl]-1-azoniabicyclo[2.2.2]octane; bromide (R)-3-[(3,4-Difluorobenzyl)-(3-fluorophenyl)carbamoyloxy]-1-[2-(4-fluorophenoxy)ethyl]-1-azoniabicyclo[2.2.2]octane; bromide (R)-3-[(3,4-Difluorobenzyl)-(3-fluorophenyl)carbamoyloxy]-1-(2-phenylsulfanylethyl)-1-azoniabicyclo[2.2.2]octane; chloride (R)-3-[(3,4-Difluorobenzyl)-(3-fluorophenyl)carbamoyloxy]-1-(3-phenoxypropyl)-1-azoniabicyclo[2.2.2]octane; bromide (R)-3-[(3,4-Difluorobenzyl)-(3-fluorophenyl)carbamoyloxy]-1-[3-(4-fluorophenoxy)propyl]-1-azoniabicyclo[2.2.2]octane; chloride (R)-3-[(2-Fluorophenyl)-(3,4,5-trifluorobenzyl)carbamoyloxy]-1-phenethyl-1-azoniabicyclo[2.2.2]octane; bromide (R)-3-[(2-Fluorophenyl)-(3,4,5-trifluorobenzyl)carbamoyloxy]-1-[2-(4-methoxyphenyl)ethyl]-1-azoniabicyclo[2.2.2]octane; chloride (R)-3-[(2-Fluorophenyl)-(3,4,5-trifluorobenzyl)carbamoyloxy]-1-(2-phenoxyethyl)-1-azoniabicyclo[2.2.2]octane; bromide (R)-1-[2-(4-Fluorophenoxy)ethyl]-3-[(2-fluorophenyl)-(3,4,5-trifluorobenzyl)carbamoyloxy]-1-azoniabicyclo[2.2.2]octane; bromide (R)-3-[(2-Fluorophenyl)-(3,4,5-trifluorobenzyl)carbamoyloxy]-1-(3-phenylpropyl)-1-azoniabicyclo[2.2.2]octane; bromide (R)-3-[(3-Fluorophenyl)-(3,4,5-trifluorobenzyl)carbamoyloxy]-1-phenethyl-1-azoniabicyclo[2.2.2]octane; bromide (R)-1-[2-(2-Fluorophenyl)ethyl]-3-[(3-fluorophenyl)-(3,4,5-trifluorobenzyl)carbamoyloxy]-1-azoniabicyclo[2.2.2]octane; bromide (R)-3-[(3-Fluorophenyl)-(3,4,5-trifluorobenzyl)carbamoyloxy]-1-[2-(4-methoxyphenyl)ethyl]-1-azoniabicyclo[2.2.2]octane; chloride (R)-1-[2-(2,3-Dihydrobenzofuran-5-yl)ethyl]-3-[(3-fluorophenyl)-(3,4,5-trifluorobenzyl)carbamoyloxy]-1-azoniabicyclo[2.2.2]octane; bromide (R)-3-[(3-Fluorophenyl)-(3,4,5-trifluorobenzyl)carbamoyloxy]-1-(2-phenoxyethyl)-1-azoniabicyclo[2.2.2]octane; bromide (R)-1-[2-(4-Fluorophenoxy)ethyl]-3-[(3-fluorophenyl)-(3,4,5-trifluorobenzyl)carbamoyloxy]-1-azoniabicyclo[2.2.2]octane; bromide (R)-3-[(3-Fluorophenyl)-(3,4,5-trifluorobenzyl)carbamoyloxy]-1-(2-phenylsulfanylethyl)-1-azoniabicyclo[2.2.2]octane; chloride (R)-3-[(3-Fluorophenyl)-(3,4,5-trifluorobenzyl)carbamoyloxy]-1-(3-phenylpropyl)-1-azoniabicyclo[2.2.2]octane; bromide (R)-1-Cyclobutylmethyl-3-(thiophen-2-ylmethyl-m-tolylcarbamoyloxy)-1-azoniabicyclo[2.2.2]octane; bromide (R)-1-Phenethyl-3-(thiophen-2-ylmethyl-m-tolylcarbamoyloxy)-1-azoniabicyclo[2.2.2]octane; bromide (R)-1-[2-(2,3-Dihydrobenzofuran-5-yl)ethyl]-3-(thiophen-2-ylmethyl-m-tolylcarbamoyloxy)-1-azoniabicyclo[2.2.2]octane; bromide (R)-1-(2-Thiophen-2-ylethyl)-3-(thiophen-2-ylmethyl-m-tolylcarbamoyloxy)-1-azoniabicyclo[2.2.2]octane; bromide (R)-1-(3-Phenoxypropyl)-3-(thiophen-2-ylmethyl-m-tolylcarbamoyloxy)-1-azoniabicyclo[2.2.2]octane; bromide (R)-1-Cyclopropylmethyl-3-[(2-fluorophenyl)thiophen-2-ylmethylcarbamoyloxy]-1-azoniabicyclo[2.2.2]octane; bromide (R)-3-[(2-Fluorophenyl)thiophen-2-ylmethylcarbamoyloxy]-1-phenethyl-1-azoniabicyclo[2.2.2]octane; bromide (R)-3-[(2-Fluorophenyl)thiophen-2-ylmethylcarbamoyloxy]-1-[2-(4-methoxyphenyl)ethyl]-1-azoniabicyclo[2.2.2]octane; chloride (R)-3-[(2-Fluorophenyl)thiophen-2-ylmethylcarbamoyloxy]-1-(2-phenoxyethyl)-1-azoniabicyclo[2.2.2]octane; bromide (R)-3-[(2-Fluorophenyl)thiophen-2-ylmethylcarbamoyloxy]-1-(2-phenylsulfanylethyl)-1-azoniabicyclo[2.2.2]octane; chloride
(R)-3-[(2-Fluorophenyl)thiophen-2-ylmethylcarbamoyloxy]-1-(3-phenylpropyl)-1-azoniabicyclo[2.2.2]octane; bromide
(R)-3-[(2-Fluorophenyl)thiophen-2-ylmethylcarbamoyloxy]-1-(3-phenoxypropyl)-1-azoniabicyclo[2.2.2]octane; bromide
(R)-1-Benzyl-3-[(3-fluorophenyl)thiophen-2-ylmethylcarbamoyloxy]-1-azoniabicyclo[2.2.2]octane; bromide
(R)-3-[(3-Fluorophenyl)thiophen-2-ylmethylcarbamoyloxy]-1-phenylsulfanylmethyl-1-azoniabicyclo[2.2.2]octane; chloride
(R)-3-[(3-Fluorophenyl)thiophen-2-ylmethylcarbamoyloxy]-1-[2-(4-methoxyphenyl)ethyl]-1-azoniabicyclo[2.2.2]octane; bromide
(R)-[1-[2-(2,3-Dihydrobenzofuran-5-yl)ethyl]-3-[(3-fluorophenyl)thiophen-2-ylmethylcarbamoyloxy]-1-azoniabicyclo[2.2.2]octane; bromide
(R)-3-[(3-Fluorophenyl)thiophen-2-ylmethylcarbamoyloxy]-1-(3-phenylpropyl)-1-azoniabicyclo[2.2.2]octane; bromide
(R)-3-[(3-Fluorophenyl)thiophen-2-ylmethylcarbamoyloxy]-1-(3-phenoxypropyl)-1-azoniabicyclo[2.2.2]octane; bromide
(R)-3-[(4-Bromothiophen-2-ylmethyl)phenylcarbamoyloxy]-1-phenethyl-1-azoniabicyclo[2.2.2]octane; bromide
(R)-3-[(4-Bromothiophen-2-ylmethyl)phenylcarbamoyloxy]-1-(2-oxo-2-phenylethyl)-1-azoniabicyclo[2.2.2]octane; bromide
(R)-3-[(4-Bromothiophen-2-ylmethyl)phenylcarbamoyloxy]-1-(2-phenoxyethyl)-1-azoniabicyclo[2.2.2]octane; bromide
(R)-3-[(4-Bromothiophen-2-ylmethyl)phenylcarbamoyloxy]-1-(2-phenylsulfanylethyl)-1-azoniabicyclo[2.2.2]octane; chloride
(R)-3-[(4-Bromothiophen-2-ylmethyl)phenylcarbamoyloxy]-1-(3-phenylpropyl)-1-azoniabicyclo[2.2.2]octane; bromide
(R)-3-[(4-Bromothiophen-2-ylmethyl)phenylcarbamoyloxy]-1-(3-phenoxypropyl)-1-azoniabicyclo[2.2.2]octane; bromide
(R)-3-[(5-Methylthiophen-2-ylmethyl)phenylcarbamoyloxy]-1-(2-phenoxyethyl)-1-azoniabicyclo[2.2.2]octane; bromide
(R)-3-[(5-Bromothiophen-2-ylmethyl)phenylcarbamoyloxy]-1-phenylsulfanylmethyl-1-azoniabicyclo[2.2.2]octane; chloride
(R)-3-[(5-Bromothiophen-2-ylmethyl)phenylcarbamoyloxy]-1-phenethyl-1-azoniabicyclo[2.2.2]octane; bromide
(R)-3-[(5-Bromothiophen-2-ylmethyl)phenylcarbamoyloxy]-1-(2-oxo-2-phenylethyl)-1-azoniabicyclo[2.2.2]octane; bromide
(R)-3-[(5-Bromothiophen-2-ylmethyl)phenylcarbamoyloxy]-1-(2-phenoxyethyl)-1-azoniabicyclo[2.2.2]octane; bromide
(R)-3-[(5-Bromothiophen-2-ylmethyl)phenylcarbamoyloxy]-1-(3-phenylpropyl)-1-azoniabicyclo[2.2.2]octane; bromide
(R)-3-[(5-Bromothiophen-2-ylmethyl)phenylcarbamoyloxy]-1-(3-phenoxypropyl)-1-azoniabicyclo[2.2.2]octane; bromide
(R)-3-[(5-Bromothiophen-2-ylmethyl)-m-tolylcarbamoyloxy]-1-(2-phenoxyethyl)-1-azoniabicyclo[2.2.2]octane; bromide
(R)-3-[(5-Bromothiophen-2-ylmethyl)-m-tolylcarbamoyloxy]-1-(2-phenylsulfanylethyl)-1-azoniabicyclo[2.2.2]octane; bromide
(R)-3-[(5-Bromothiophen-2-ylmethyl)-m-tolylcarbamoyloxy]-1-(3-phenoxypropyl)-1-azoniabicyclo[2.2.2]octane; bromide
(R)-3-[(3-Fluorophenyl)thiophen-3-ylmethylcarbamoyloxy]-1-phenethyl-1-azoniabicyclo[2.2.2]octane; bromide
(R)-1-[2-(2,3-Dihydrobenzofuran-5-yl)ethyl]-3-[(3-fluorophenyl)thiophen-3-ylmethylcarbamoyloxy]-1-azoniabicyclo[2.2.2]octane; bromide
(R)-3-[(3-Fluorophenyl)thiophen-3-ylmethylcarbamoyloxy]-1-(2-phenoxyethyl)-1-azoniabicyclo[2.2.2]octane
(R)-3-[(3-Fluorophenyl)thiophen-3-ylmethylcarbamoyloxy]-1-(3-phenoxypropyl)-1-azoniabicyclo[2.2.2]octane; bromide

The invention claimed is:
1. A compound of general formula (I)

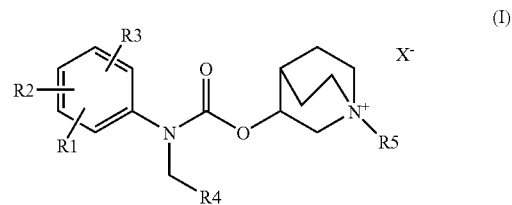

and individual isomers, racemic or non-racemic mixtures of isomers, and pharmaceutically acceptable salts thereof,
wherein R1, R2 and R3 are radicals independently selected from the group consisting of H, OH, $NO_2$, SH, CN, F, Cl, Br, I, COOH, $CONH_2$, ($C_1$-$C_4$)-alkoxycarbonyl, ($C_1$-$C_4$)-alkylsulfanyl, ($C_1$-$C_4$)-alkylsulfinyl, ($C_1$-$C_4$)-alkylsulfonyl, ($C_1$-$C_4$)-alkoxyl optionally substituted with one or several F, and ($C_1$-$C_4$)-alkyl optionally substituted with one or several F or OH; alternatively, either R1 and R2, or R2 and R3 may be forming a biradical selected from the group consisting of —$CH_2$—$CH_2$—$CH_2$—, and —$CH_2$—$CH_2$—$CH_2$—$CH_2$—;
R4 is a radical selected from the group consisting of:
a) a C-linked radical of a five or six membered heterocyclic ring containing at least one heteroatom selected from the group consisting of O, S, and N, being this heterocyclic ring substituted with one or several substituents independently selected from the group consisting of OH, oxo (═O), SH, $NO_2$, CN, F, Cl, Br, I, $CONH_2$, COOH, ($C_1$-$C_4$)-alkoxycarbonyl, ($C_1$-$C_4$)-alkylsulfanyl, ($C_1$-$C_4$)-alkylsulfinyl, ($C_1$-$C_4$)-alkylsulfonyl, ($C_1$-$C_4$)-alkyl optionally substituted with one or several F or OH, and ($C_1$-$C_4$)-alkoxyl optionally substituted with one or several F;
b) a C-linked radical of a bicyclic ring system consisting of a phenyl ring fused to a five or six membered heterocyclic ring containing at least one heteroatom selected from the group consisting of O, S and N, being this bicyclic ring system optionally substituted with one or several substituents independently selected from the group consisting of OH, oxo (═O), SH, $NO_2$, CN, F, Cl, Br, I, $CONH_2$, COOH, ($C_1$-$C_4$)-alkoxycarbonyl, ($C_1$-$C_4$)-alkylsulfanyl, ($C_1$-$C_4$)-alkylsulfinyl, ($C_1$-$C_4$)-alkylsulfonyl, ($C_1$-$C_4$)-alkyl optionally substituted with one or several F or OH, and ($C_1$-$C_4$)-alkoxyl optionally substituted with one or several F; and c) phenyl substituted with one or several substituents independently selected from the group consisting of OH, SH, NO$_2$, CN, F, Cl, Br, I, CONH$_2$, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;

R5 is a radical selected from the group consisting of:
a) cyclopropyl, cyclobutyl, cyclopentyl, cyclohexyl, all of them optionally substituted with one or several substituents independently selected from the group consisting of OH, oxo (═O), SH, NO$_2$, CN, F, Cl, Br, I, CONH$_2$, NR7CO—(C$_1$-C$_4$)-alkyl, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
b) (C$_1$-C$_{10}$)-alkyl substituted with one or several radicals independently selected from the group consisting of R6, COR6, NH$_2$, NR6R7, CONR6R7, NR7COR6, OH, OR6, COOR6, OCOR6, SO$_2$R6, SH, SR6, SOR6, COSR6, SCOR6, CN, F, Cl, Br, NO$_2$, cyclopropyl, cyclobutyl, cyclopentyl, cyclohexyl, cyclohexenyl, norbornenyl, and bicyclo[2.2.1] heptanyl;

R6 is a radical selected from the group consisting of:
a) (C$_1$-C$_5$)-alkyl, cyclopropyl, cyclobutyl, cyclopentyl, cyclohexyl, cyclohexenyl, norbornenyl, bicyclo[2.2.1] heptanyl, all of them optionally substituted with one or several substituents independently selected from the group consisting of OH, oxo (═O), SH, NO$_2$, CN, F, Cl, Br, I, CONH$_2$, NR7CO—(C$_1$-C$_4$)-alkyl, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
b) phenyl optionally substituted with one or several substituents independently selected from the group consisting of OH, SH, NO$_2$, CN, F, Cl, Br, I, CONH$_2$, NR7CO—(C$_1$-C$_4$)-alkyl, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
c) a C-linked radical of a five or six membered heterocyclic ring containing at least one heteroatom selected from the group consisting of O, S, and N, being this heterocyclic ring optionally substituted with one or several substituents independently selected from the group consisting of OH, oxo (═O), SH, NO$_2$, CN, F, Cl, Br, I, CONH$_2$, NR7CO—(C$_1$-C$_4$)-alkyl, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F; and
d) a C-linked radical of a bicyclic ring system consisting of a phenyl fused to a five or six membered heterocyclic ring containing at least one heteroatom selected from the group consisting of O, S and N, being this bicyclic ring system optionally substituted with one or several substituents independently selected from the group consisting of OH, oxo (═O), SH, NO$_2$, CN, F, Cl, Br, I, CONH$_2$, COOH, NR7CO—(C$_1$-C$_4$)-alkyl, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;

R7 is a radical selected from the group consisting of H, phenoxycarbonyl, benzyloxycarbonyl, (C$_1$-C$_4$)-alkoxycarbonyl, (C$_1$-C$_4$)-alkylcarbonyl, (C$_1$-C$_4$)-alkylsulfonyl, and (C$_1$-C$_5$)-alkyl; and X$^-$ is a physiologically acceptable anion.

2. A compound according to claim 1, wherein R4 is a thiophene substituted with one or several substituents independently selected from the group consisting of OH, SH, NO$_2$, CN, F, Cl, Br, I, CONH$_2$, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F.

3. A compound according to claim 1, wherein R4 is a phenyl substituted with one or several substituents independently selected from the group consisting of OH, SH, NO$_2$, CN, F, Cl, Br, I, CONH$_2$, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F.

4. A compound according to claim 1, wherein
R5 is a (C$_1$-C$_5$)-alkyl substituted with one radical selected from the group consisting of R6, COR6, NR6,R7, CONR6,R7, NR7COR6, OR6, COOR6, OCOR6, SR6, SOR6, SO$_2$R6; and
R6 is a radical selected from the group consisting of:
a) phenyl optionally substituted with one or several substituents selected from the group consisting of OH, SH, CN, F, Cl, Br, I, CONH$_2$, COOH, (C$_1$-C$_4$)-alkoxycarbonyl, (C$_1$-C$_4$)alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F;
b) a C-linked radical of a five or six membered heterocyclic ring containing at least one heteroatom selected from the group consisting of O, S, and N, being this heterocyclic ring optionally substituted with one or several substituents independently selected from the group consisting of OH, SH, NO$_2$, CN, F, Cl, Br, I, CONH$_2$, COOH, (C$_1$-C$_4$)-alkoxycarbonyl, (C$_1$-C$_4$)-alkylsulfanyl, (C$_1$-C$_4$)-alkylsulfinyl, (C$_1$-C$_4$)-alkylsulfonyl, (C$_1$-C$_4$)-alkyl optionally substituted with one or several F or OH, and (C$_1$-C$_4$)-alkoxyl optionally substituted with one or several F.

5. Intermediate compound of formula (X)

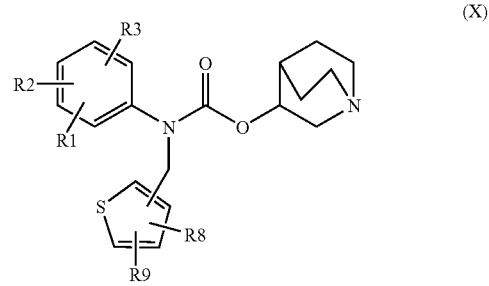

and individual isomers, racemic or non-racemic mixtures of isomers, and pharmaceutically acceptable salts thereof, for the preparation of a compound of formula (I) as defined in claim 1, wherein R1, R2, R3, R8 and R9 are radicals independently selected from the group consisting of H, OH, $NO_2$, SH, CN, F, Cl, Br, I, $CONH_2$, COOH, $(C_1\text{-}C_4)$-alkoxycarbonyl, $(C_1\text{-}C_4)$-alkylsulfanyl, $(C_1\text{-}C_4)$-alkylsulfinyl, $(C_1\text{-}C_4)$-alkylsulfonyl, $(C_1\text{-}C_4)$-alkoxyl optionally substituted with one or several F, and $(C_1\text{-}C_4)$-alkyl optionally substituted with one or several F or OH, except when R8 and R9 are H; alternatively, either R1 and R2, or R2 and R3 may be forming a biradical selected from the group consisting of $-CH_2-CH_2-CH_2-$, and $-CH_2-CH_2-CH_2-CH_2-$.

6. A compound according to claim 1, wherein the configuration of the 3 position in the quinuclidine ring is (R).

7. A method of treating urinary incontinence in a subject comprising administering to the subject in need thereof a therapeutic amount of a compound according to claim 1.

8. The method according to claim 7, wherein urinary incontinence is caused by overactive bladder.

9. A method of treating irritable bowel syndrome in a subject comprising administering to the subject in need thereof a therapeutic amount of a compound according to claim 1.

10. A method of treating a respiratory disease in a subject comprising administering to the subject in need thereof a therapeutic amount of a compound according to claim 1, wherein the disease is selected from the group consisting of chronic obstructive pulmonary disease, chronic bronchitis, asthma, emphysema, and rhinitis.

11. A method of treating an ophthalmic intervention in a subject comprising administering to the subject in need thereof a therapeutic amount of a compound according to claim 1, wherein administration induces mydriasis and cycloplegia.

12. A pharmaceutical composition comprising an effective amount of a compound of claim 1 and a pharmaceutically acceptable excipient.

\* \* \* \* \*